United States Patent
Khurana et al.

(10) Patent No.: US 11,835,510 B2
(45) Date of Patent: *Dec. 5, 2023

(54) OBTAINING INFORMATION FROM A BIOLOGICAL SAMPLE IN A FLOW CELL

(71) Applicant: ILLUMINA, INC., San Diego, CA (US)

(72) Inventors: Tarun Khurana, Freemont, CA (US); Ali Agah, Menlo Park, CA (US); Aathavan Karunakaran, Berkeley, CA (US); Xi-Jun Chen, Belmont, CA (US)

(73) Assignee: ILLUMINA, INC., San Diego, CA (US)

( * ) Notice: Subject to any disclaimer, the term of this patent is extended or adjusted under 35 U.S.C. 154(b) by 145 days.

This patent is subject to a terminal disclaimer.

(21) Appl. No.: 17/470,228

(22) Filed: Sep. 9, 2021

(65) Prior Publication Data

US 2021/0405019 A1     Dec. 30, 2021

Related U.S. Application Data

(62) Division of application No. 17/254,473, filed as application No. PCT/US2020/034514 on May 26, 2020, now Pat. No. 11,137,385.

(60) Provisional application No. 62/855,622, filed on May 31, 2019.

(51) Int. Cl.
| | | |
|---|---|---|
| *C12Q 1/00* | (2006.01) | |
| *G01N 33/483* | (2006.01) | |
| *G01N 33/50* | (2006.01) | |
| *G01N 33/53* | (2006.01) | |
| *A61K 39/12* | (2006.01) | |

(52) U.S. Cl.
CPC ..... *G01N 33/4836* (2013.01); *G01N 33/5047* (2013.01); *G01N 33/5308* (2013.01); *A61K 39/12* (2013.01); *G01N 2500/10* (2013.01)

(58) Field of Classification Search
CPC .................................................. G01N 33/4836
See application file for complete search history.

(56) References Cited

U.S. PATENT DOCUMENTS

| | | |
|---|---|---|
| 7,414,116 B2 | 8/2008 | Milton et al. |
| 8,906,320 B1 | 12/2014 | Eltoukhy et al. |
| 9,012,022 B2 | 4/2015 | George et al. |
| 9,453,258 B2 | 9/2016 | Kain et al. |
| 9,512,422 B2 | 12/2016 | Barnard et al. |
| 10,254,225 B2 | 4/2019 | Zhong et al. |
| 11,137,385 B2 * | 10/2021 | Khurana ............ G01N 33/5308 |
| 11,453,003 B2 * | 9/2022 | Agah ..................... G11C 13/02 |
| 2007/0042372 A1 | 2/2007 | Arita |
| 2014/0342360 A1 | 11/2014 | Faham et al. |
| 2015/0261664 A1 | 9/2015 | Goldman et al. |
| 2018/0117587 A1 | 5/2018 | Lemoine et al. |

FOREIGN PATENT DOCUMENTS

| | | |
|---|---|---|
| WO | WO 2015/103225 A1 | 7/2015 |
| WO | WO 2016/130704 A2 | 8/2016 |
| WO | WO 2017/011492 A1 | 1/2017 |

OTHER PUBLICATIONS

Shipman, Seth L., et al. "CRISPR—Cas encoding of a digital movie into the genomes of a population of living bacteria." *Nature* 547.7663 (2017): 345-349.

Yassai, Maryam B., et al. "A clonotype nomenclature for T cell receptors." *Immunogenetics* 61.7 (2009): 493-502.

International Search Report and Written Opinion dated Aug. 25, 2020 for International Application No. PCT/US2020/034514, 10 pages.

* cited by examiner

*Primary Examiner* — Albert M Navarro

(74) *Attorney, Agent, or Firm* — FROST BROWN TODD LLP

(57) ABSTRACT

Methods are used for obtaining, cataloguing, and/or storing data derived from a biological source using a flow cell body, electrodes, and an imaging assembly. The data may include DNA and/or RNA obtained from a biological source, such as from the cells of an organism. The methods may be used to obtain, catalog, and/or store data such as DNA or RNA sequence from a pathogen such as a virus and/or a bacteria, human health data over time, and immune system information from an individual. The data obtained using the disclosed methods may be used for a variety of different purposes, including the manufacture of vaccine compositions, and for restoring the immune system of an individual who has undergone an immune system depleting event. The methods may be used for storage of biological cells, which may be used for the screening of compounds, such as small molecules with potential for therapeutic indications.

21 Claims, 7 Drawing Sheets

OBTAINING INFORMATION FROM A BIOLOGICAL SAMPLE IN A FLOW CELL

RELATED APPLICATION

This application is a divisional of U.S. patent application Ser. No. 17/254,473, entitled "Obtaining Information from a Biological Sample in a Flow Cell," filed on Dec. 21, 2020, which is a national stage entry of International Patent Application No. PCT/US2020/034514, entitled "Obtaining Information from a Biological Sample in a Flow Cell," filed on May 26, 2020, which claims priority to U.S. Provisional Patent App. No. 62/855,622, entitled "Obtaining Information from a Biological Sample in a Flow Cell," filed on May 31, 2019, which is incorporated by reference herein in its entirety.

BACKGROUND

Computer systems have used various different mechanisms to store data, including magnetic storage, optical storage, and solid-state storage. Such forms of data storage may present drawbacks in the form of read-write speed, duration of data retention, power usage, or data density.

Just as naturally occurring DNA may be read, machine-written DNA may also be read. Pre-existing DNA reading techniques may include an array-based, cyclic sequencing assay (e.g., sequencing-by-synthesis (SBS)), where a dense array of DNA features (e.g., template nucleic acids) are sequenced through iterative cycles of enzymatic manipulation. After each cycle, an image may be captured and subsequently analyzed with other images to determine a sequence of the machine-written DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

SUMMARY

Described herein are devices, systems, and methods for obtaining and optionally catalogue sequences directly from biological samples.

An implementation relates to implementation relates to a method comprising contacting a biological sample with an apparatus, the apparatus comprising a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth, a plurality of electrodes, each electrode of the plurality of electrodes being positioned in a corresponding well of the plurality of wells, the plurality of electrodes to effect one or both of reading or writing of a polynucleotide in the corresponding well of the plurality of wells, and an imaging assembly to capture images indicative of the nucleotide in a polynucleotide written in at least one well of the plurality of wells; obtaining information by one or both of reading or writing of said polynucleotide; wherein said contacting comprises contacting said biological sample with the flow cell body of said apparatus; and wherein said information is a DNA or RNA sequence contained within said biological sample.

Variations on any one or more of the above implementations exist, wherein the method may further comprise storing the information.

Variations on any one or more of the above implementations exist, wherein the information may be selected from one or both of a DNA sequence from a biological sample, and an RNA sequence from a biological sample, wherein the polynucleotide corresponds to one or both of the DNA sequence of the biological sample and the RNA sequence from the biological sample.

Variations on any one or more of the above implementations exist, wherein the one or both of RNA and DNA may be cell-free DNA or cell-free RNA.

Variations on any one or more of the above implementations exist, wherein the biological sample may be selected from whole blood, serum, plasma, or combinations thereof.

Variations on any one or more of the above implementations exist, wherein the biological sample may be selected from one or both of a virus and a bacteria.

Variations on any one or more of the above implementations exist, wherein the method may comprise incorporating a location indexing feature, wherein the location indexing feature may be used to identify the location of the information on the apparatus.

Variations on any one or more of the above implementations exist, wherein the location indexing feature may comprise a predetermined sequence affixed to the apparatus, wherein the predetermined sequence may be incorporated into the polynucleotide.

Variations on any one or more of the above implementations exist, wherein the method may further comprise incorporating a source indexing feature, wherein the source indexing feature may be used to identify the source of the information on the apparatus.

Variations on any one or more of the above implementations exist, wherein the source indexing feature may comprise a predetermined sequence that is incorporated into the polynucleotide.

Another implementation relates to a method comprising contacting a biological sample with an apparatus, the apparatus comprising: a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth, a plurality of electrodes, each electrode of the plurality of electrodes being positioned in a corresponding well of the plurality of wells, the plurality of electrodes to effect one or both of reading and writing of a polynucleotide in the corresponding well of the plurality of wells, an imaging assembly to capture images indicative of the nucleotide in a polynucleotide written in at least one well of the plurality of wells, and one or more binding components positioned in or approximate to the plurality of wells, the one or more binding components to selectively bind with a biological cell in said biological sample; wherein said contacting comprises contacting said biological sample with the flow cell body of said apparatus to bind said binding component with said biological cell, wherein said binding affixes said biological cell to said apparatus.

Variations on any one or more of the above implementations exist, wherein the binding component may be used to bind to a preselected cell type, wherein the binding component may be selective for the preselected cell type.

Variations on any one or more of the above implementations exist, wherein the binding component may bind to a surface molecule of a biological cell, wherein the surface molecule may be selected from a protein, a peptide, a receptor, a sugar molecule, or combinations thereof.

Variations on any one or more of the above implementations exist, wherein the binding component may be selected from a nucleotide, a protein, a peptide, a small molecule, or combinations thereof.

Variations on any one or more of the above implementations exist, wherein the information obtained from the biological cell may be selected from a DNA sequence from the biological cell, an RNA sequence from the biological cell, the type of the biological cell, or combinations thereof.

Variations on any one or more of the above implementations exist, wherein the biological sample may be selected from whole blood, serum, plasma, or combinations thereof.

Variations on any one or more of the above implementations exist, wherein the method may further comprise contacting the apparatus with a first solution for separating non-affixed cells from and apparatus-affixed cells.

Variations on any one or more of the above implementations exist, wherein the method may comprise contacting the apparatus with a second solution sufficient to lyse flow-cell affixed cells, wherein the lysing exposes one or both of DNA and RNA for writing of the polynucleotide contained within the apparatus-affixed cells.

Variations on any one or more of the above implementations exist, wherein the method may comprise binding a plurality of biological cells in the apparatus and flowing in a fluid for storage of the plurality of biological cells.

Variations on any one or more of the above implementations exist, wherein the fluid for storage may be a culture medium.

Variations on any one or more of the above implementations exist, wherein the method may comprise reading the information in the polynucleotide.

Another implementation relates to a method comprising writing a nucleotide sequence of interest; integrating the written nucleotide sequence into a genome of a biological cell; and storing said biological cell in an apparatus, the apparatus comprising: a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth, a plurality of electrodes, each electrode of the plurality of electrodes being positioned in a corresponding well of the plurality of wells, the plurality of electrodes to effect one or both of reading or writing of a polynucleotide in the corresponding well of the plurality of wells, and an imaging assembly to capture images indicative of the nucleotide in a polynucleotide written in at least one well of the plurality of wells.

Variations on any one or more of the above implementations exist, wherein the method may comprise harvesting the nucleotide sequence of interest from the biological cell.

Another implementation relates to a method of storing a health record of an individual over time. In this implementation, the method may comprise obtaining biological information of an individual according to an implementation described in the second through twenty-third paragraphs in this summary.

Variations on any one or more of the above implementations exist, wherein the writing, integrating, and storing is repeated.

Another implementation relates to a method for storing the biological information of a species, and may comprise obtaining the biological information of the species according to an implementation of any of paragraphs two through twenty-one.

Another implementation relates to a method comprising contacting a biological sample from said individual with an apparatus, the apparatus comprising a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth, a plurality of electrodes, each electrode of the plurality of electrodes being positioned in a corresponding well of the plurality of wells, the plurality of electrodes to effect one or both of reading and writing of a polynucleotide in the corresponding plurality of wells, and an imaging assembly to capture images indicative of the nucleotide in a polynucleotide written in at least one well of the plurality of wells; obtaining information from said biological sample; and cataloging said information from said biological sample.

Variations on any one or more of the above implementations exist, wherein the biological sample may comprise lymphocytes from said individual.

Variations on any one or more of the above implementations exist, wherein the cataloging may comprise obtaining a clonotype profile from the individual, wherein the clonotype may comprise at least a portion of a VDJ region of a B cell receptor of said individual.

Variations on any one or more of the above implementations exist, wherein the cataloging may comprise obtaining a clonotype profile from said individual, wherein each clonotype may comprise at least a portion of a C gene segment from said individual.

Variations on any one or more of the above implementations exist, wherein the method may comprise obtaining a sample of nucleic acids from lymphocytes of an individual.

Variations on any one or more of the above implementations exist, wherein the sample may comprise one or more sequences selected from a portion of a C gene segment of a B cell receptor, a VDJ region of a B cell receptor, or combinations thereof.

Variations on any one or more of the above implementations exist, wherein the lymphocytes may be lysed at a time point selected from prior to contact, during contact, after contact with an apparatus as described in this summary, or combinations thereof.

Variations on any one or more of the above implementations exist, wherein the method may comprise primers to amplify a clonotype of an individual.

Variations on any one or more of the above implementations exist, wherein the apparatus may comprise one or more primers to amplify a region selected from a variable (V) region, a constant (C) region, a diversity (D) region, a joining (J) region, and combinations thereof.

Variations on any one or more of the above implementations exist, wherein the cataloguing may comprise recording VDJ information from immune cells of said individual.

Variations on any one or more of the above implementations exist, wherein said individual has not undergone an immune-system depleting event.

Variations on any one or more of the above implementations exist, wherein the method may comprise using the catalogued information to restore the immune system of an individual who has undergone an immune-system depleting event.

Variations on any one or more of the above implementations exist, wherein the immune-system depleting event may be a chemotherapy treatment.

Variations on any one or more of the above implementations exist, wherein the method may comprise causing electroporation or lysis of a biological cell within said flow cell body using an electrode.

Another implementation relates to a method of creating a vaccine, which may comprise contacting a viral pathogen with a flow cell comprising primers that is to bind to said viral pathogen; writing a nucleotide sequence of said viral pathogen to said flow cell; and storing said viral pathogen to said flow cell.

Variations on any one or more of the above implementations exist, wherein the method may comprise fragmenting the viral pathogen prior to contacting.

Variations on any one or more of the above implementations exist, wherein the method may comprise reading a viral pathogen from a flow cell, wherein the reading generates viral fragments, and wherein the viral fragments comprise a vaccine composition.

It should be appreciated that all combinations of the foregoing concepts and additional concepts discussed in greater detail below (provided such concepts are not mutually inconsistent) are contemplated as being part of the inventive subject matter disclosed herein and to achieve the benefits/advantages as described herein. In particular, all combinations of claimed subject matter appearing at the end of this disclosure are contemplated as being part of the inventive subject matter disclosed herein.

BRIEF DESCRIPTION OF THE DRAWINGS

The details of one or more implementations are set forth in the accompanying drawings and the description below. Other features, aspects, and advantages will become apparent from the description, the drawings, and the claims, in which:

Figure 1:
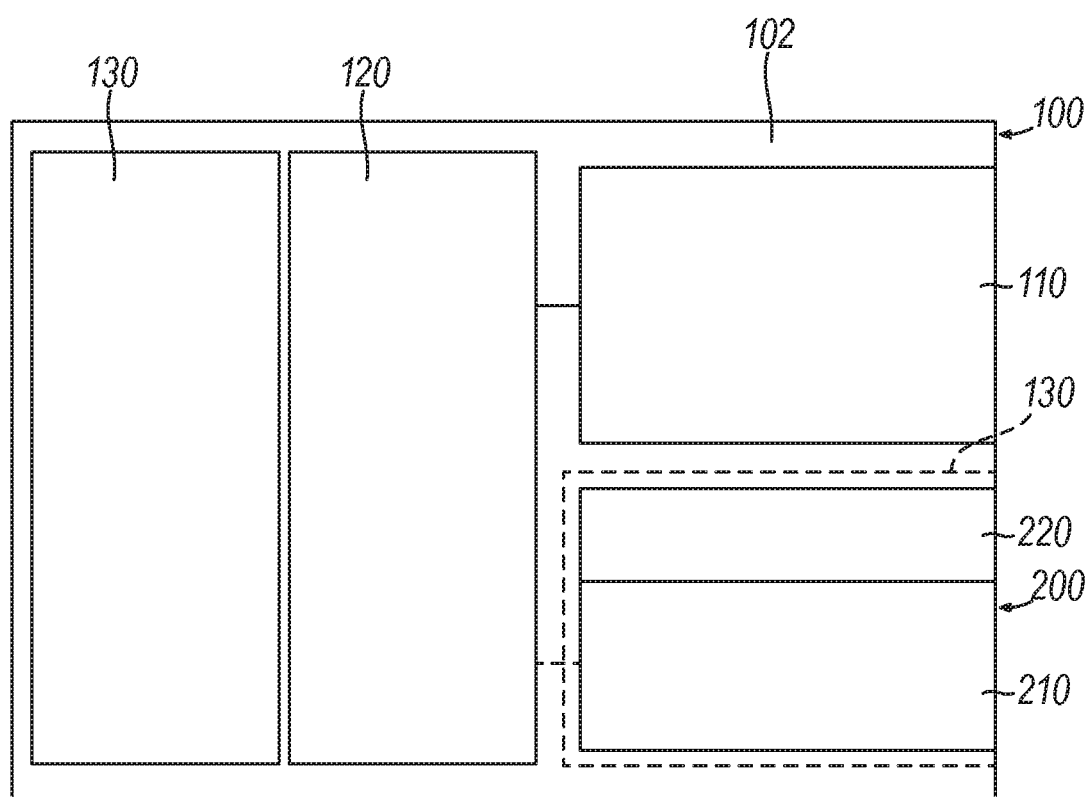
FIG. 1 depicts a block schematic view of an example of a system that may be used to conduct biochemical processes.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

In some aspects, methods and systems are disclosed herein for the obtaining, cataloging, and/or storing of biological data (or other biological material), as well as retrieving such data or other information. Machine-written DNA may provide an alternative to traditional forms of data storage (e.g., magnetic storage, optical storage, and solid-state storage). Machine-written DNA may provide faster read-write speeds, longer data retention, reduced power usage, and higher data density. Examples of how digital information may be stored in DNA are disclosed in U.S. Pub. No. 2015/0261664, entitled "High-Capacity of Storage of Digital Information in DNA," published Sep. 17, 2015, which is incorporated by reference herein in its entirety. For example, methods from code theory to enhance the recoverability of the encoded messages from the DNA segment, including forbidding DNA homopolymers (i.e. runs of more than one identical base) that are known to be associated with higher error rates in existing high throughput technologies may be used. Further, an error-detecting component, analogous to a parity-check bit, may be integrated into the indexing information in the code. More complex schemes, including but not limited to error-correcting codes and, indeed, substantially any form of digital data security (e.g., RAID-based schemes) currently employed in informatics, may be implemented in future developments of the DNA storage scheme. The DNA encoding of information may be computed using software. The bytes comprising each computer file may be represented by a DNA sequence with no homopolymers by an encoding scheme to produce an encoded file that replaces each byte by five or six bases forming the DNA sequence.

The code used in the encoding scheme may be constructed to permit a straightforward encoding that is close to the optimum information capacity for a run length-limited channel (e.g., no repeated nucleotides), though other encoding schemes may be used. The resulting in silico DNA sequences may be too long to be readily produced by standard oligonucleotide synthesis and may be split into overlapping segments of a length of 100 bases with an overlap of 75 bases. To reduce the risk of systematic synthesis errors introduced to any particular run of bases, alternate ones of the segments may be converted to their reverse complement, meaning that each base may be "written" four times, twice in each direction. Each segment may then be augmented with an indexing information that permits determination of the computer file from which the segment originated and its location within that computer file, plus simple error-detection information. This indexing information may also be encoded in as non-repeating DNA nucleotides and appended to the information storage bases of the DNA segments. The division of the DNA segments into lengths of 100 bases with an overlap of 75 bases is purely arbitrary and illustrative, and it is understood that other lengths and overlaps may be used and is not limiting.

Other encoding schemes for the DNA segments may be used, for example to provide enhanced error-correcting properties. The amount of indexing information may be increased in order to allow more or larger files to be encoded. One extension to the coding scheme in order to avoid systematic patterns in the DNA segments may be to add change the information. One way may use the "shuffling" of information in the DNA segments, where the information may be retrieved if one knows the pattern of shuffling. Different patterns of shuffles may be used for different ones of the DNA segments. A further way is to add a degree of randomness into the information in each one of the DNA segments. A series of random digits may be used for this, using modular addition of the series of random digits and the digits comprising the information encoded in the DNA segments. The information may be retrieved by modular subtraction during decoding if one knows the series of random digits used. Different series of random digits may be used for different ones of the DNA segments The data-encoding component of each string may contain Shannon information at 5.07 bits per DNA base, which is close to the theoretical optimum of 5.05 bits per DNA base for base-4 channels with run length limited to one. The indexing implementation may permit $314=4782969$ unique data locations. Increasing the number of indexing trits (and therefore bases) used to specify file and intra-file location by just two, to 16, gives $316=43046721$ unique locations, in excess of the 16.8M that is the practical maximum for the Nested Primer Molecular Memory (NPMM) scheme.

The DNA segment designs may be synthesized in three distinct runs (with the DNA segments randomly assigned to runs) to create approx. $1.2 \times 10^7$ copies of each DNA segment design. Phosphoramidite chemistry may be used, and inkjet printing and flow cell reactor technologies in an in-situ microarray synthesis platform may be employed. The inkjet printing within an anhydrous chamber may allow the delivery of very small volumes of phosphoramidites to a confined coupling area on a 2D planar surface, resulting in the addition of hundreds of thousands of bases in parallel. Subsequent oxidation and detritylation may be carried out in a flow cell reactor. Once DNA synthesis is completed, the oligonucleotides may then be cleaved from the surface and deprotected.

Adapters may then be added to the DNA segments to enable a plurality of copies of the DNA segments to be made. A DNA segment with no adapter may require additional chemical processes to "kick start" the chemistry for the synthesis of the multiple copies by adding additional groups onto the ends of the DNA segments. Oligonucleotides may be amplified using polymerase chain reaction (PCR) methods and paired-end PCR primers, followed by bead purification and quantification. Oligonucleotides may then be sequenced to produce reads of 104 bases. The digital information decoding may then be carried out via sequencing of the central bases of each oligo from both ends and rapid computation of full-length oligos and removal of sequence reads inconsistent with the designs. Sequence reads may be decoded using computer software that exactly reverses the encoding process. Sequence reads for which the parity-check trit indicates an error or that may be unambiguously decoded or assigned to a reconstructed computer file may be discarded. Locations within every decoded file may be detected in multiple different sequenced DNA oligos, and simple majority voting may be used to resolve any discrepancies caused by the DNA synthesis or the sequencing errors.

While several examples herein are provided in the context of machine-written DNA, it is contemplated that the principles described herein may be applied to other kinds of machine-written biological material.

As used herein, the term "machine-written DNA" shall be read to include one or more strands of polynucleotides that are generated by a machine, or otherwise modified by a machine, to store data or other information. One example of the polynucleotide herein is a DNA. It is noted that while the term "DNA" in the context of DNA being read or written is used throughout this disclosure, the term is used only as a representative example of a polynucleotide and may encompass the concept of a polynucleotide. "Machine," as used herein in reference to "machine-written," may include an instrument or system specially designed for writing DNA as described in greater detail herein. The system may be non-biological or biological. In one example, the biological system may comprise, or is, a polymerase. For example, the polymerase may be terminal deoxynucleotidyl transferase (TdT). In a biological system, the process may be additionally controlled by a machine hardware (e.g., processor) or an algorithm. "Machine-written DNA" may include any polynucleotide having one or more base sequences written by a machine. While machine-written DNA is used herein as an example, other polynucleotide strands may be substituted for machine-written DNA described herein. "Machine-written DNA" may include natural bases and modifications of natural bases, including but not limited to bases modified with methylation or other chemical tags; an artificially synthesized polymer that is similar to DNA, such as peptide nucleic acid (PNA); or Morpholino DNA. "Machine-written DNA" may also include DNA strands or other polynucleotides that are formed by at least one strand of bases originating from nature (e.g., extracted from a naturally occurring organism), with a machine-written strand of bases secured thereto either in a parallel fashion or in an end-to-end fashion. In other implementations, "machine-written DNA" may be written by a biological system (e.g., enzyme) in lieu of, or in addition to, a non-biological system (e.g., the electrode machine) writing of DNA described herein. In other words, "machine-written DNA" may be written directly by a machine; or by an enzyme (e.g., polymerase) that is controlled by an algorithm and/or machine.

"Machine-written DNA" may include data that have been converted from a raw form (e.g., a photograph, a text document, etc.) into a binary code sequence using known techniques, with that binary code sequence then being converted to a DNA base sequence using known techniques, and with that DNA base sequence then being generated by a machine in the form of one or more DNA strands or other polynucleotides. Alternatively, "machine-written DNA" may be generated to index or otherwise track pre-existing DNA, to store data or information from any other source and for any suitable purpose, without necessarily requiring an intermediate step of converting raw data to a binary code.

As described in greater detail below, machine-written DNA may be written to and/or read from a reaction site. As used herein, the term "reaction site" is a localized region where at least one designated reaction may occur. A reaction site may include support surfaces of a reaction structure or substrate where a substance may be immobilized thereon. For instance, the reaction site may be a discrete region of space where a discrete group of DNA strands or other polynucleotides are written. The reaction site may permit chemical reactions that are isolated from reactions that are in adjacent reaction sites. Devices that provide machine-writing of DNA may include flow cells with wells having writing features (e.g., electrodes) and/or reading features. In some instances, the reaction site may include a surface of a reaction structure (which may be positioned in a channel of a flow cell) that already has a reaction component thereon, such as a colony of polynucleotides thereon. In some flow cells, the polynucleotides in the colony have the same sequence, being for example, clonal copies of a single stranded or double stranded template. However, in some flow cells a reaction site may contain only a single polynucleotide molecule, for example, in a single stranded or double stranded form.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

To read the machine-written DNA, one or more discrete detectable regions of reaction sites may be defined. Such detectable regions may be imageable regions, electrical detection regions, or other types of regions that may have a measurable change in a property (or absence of change in the property) based on the type of nucleotide present during the reading process.

As used herein, the term "pixel" refers to a discrete imageable region. Each imageable region may include a compartment or discrete region of space where a polynucleotide is present. In some instances, a pixel may include two or more reaction sites (e.g., two or more reaction chambers, two or more reaction recesses, two or more wells, etc.). In some other instances, a pixel may include just one reaction site. Each pixel is detected using a corresponding detection device, such as an image sensor or other light detection device. The light detection device may be manufactured using integrated circuit manufacturing processes, such as processes used to manufacture charged-coupled devices circuits (CCD) or complementary-metal-oxide semiconductor (CMOS) devices or circuits. The light detection device may thereby include, for example, one or more semiconductor materials, and may take the form of, for example, a CMOS light detection device (e.g., a CMOS image sensor) or a CCD image sensor, another type of image sensor. A CMOS image sensor may include an array of light sensors (e.g. photodiodes). In one implementation, a single image sensor may be used with an objective lens to capture several "pixels," during an imaging event. In some other implementations, each discrete photodiode or light sensor may capture a corresponding pixel. In some implementations, light sensors (e.g., photodiodes) of one or more detection devices may be associated with corresponding reaction sites. A light sensor that is associated with a reaction site may detect light emissions from the associated reaction site. In some implementations, the detection of light emissions may be done via at least one light guide when a designated reaction has occurred at the associated reaction site. In some implementations, a plurality of light sensors (e.g., several pixels of a light detection or camera device) may be associated with a single reaction site. In some implementations, a single light sensor (e.g. a single pixel) may be associated with a single reaction site or with a group of reaction sites.

As used herein, the term "synthesis" shall be read to include processes where DNA is generated by a machine to store data or other information. Thus, machine-written DNA may constitute synthesized DNA. As used herein, the terms "consumable cartridge," "reagent cartridge," "removeable cartridge," and/or "cartridge" refer to the same cartridge and/or a combination of components making an assembly for a cartridge or cartridge system. The cartridges described herein may be independent of the element with the reaction sites, such as a flow cell having a plurality of wells. In some instances, a flow cell may be removably inserted into a cartridge, which is then inserted into an instrument. In some other implementations, the flow cell may be removably inserted into the instrument without a cartridge. As used herein, the term "biochemical analysis" may include at least one of biological analysis or chemical analysis.

The term "based on" should be understood to mean that something is determined at least in part by the thing it is indicated as being "based on." To indicate that something must necessarily be completely determined by something else, it is described as being based exclusively on whatever it is completely determined by.

The term "non-nucleotide memory" should be understood to refer to an object, device or combination of devices capable of storing data or instructions in a form other than nucleotides that may be retrieved and/or processed by a device. Examples of "non-nucleotide memory" include solid state memory, magnetic memory, hard drives, optical drives and combinations of the foregoing (e.g., magneto-optical storage elements).

The term "DNA storage device" should be understood to refer to an object, device, or combination of devices configured to store data or instructions in the form of sequences of polynucleotides such as machine-written DNA. Examples of "DNA storage devices" include flow cells having addressable wells as described herein, systems comprising multiple such flow cells, and tubes or other containers storing nucleotide sequences that have been cleaved from the surface on which they were synthesized. As used herein, the term "nucleotide sequence" or "polynucleotide sequence" should be read to include a polynucleotide molecule, as well as the underlying sequence of the molecule, depending on context. A sequence of a polynucleotide may contain (or encode) information indicative of certain physical characteristics.

Implementations set forth herein may be used to perform designated reactions for consumable cartridge preparation and/or biochemical analysis and/or synthesis of machine-written DNA.

I. System Overview

FIG. 1 is a schematic diagram of a system 100 that is configured to conduct biochemical analysis and/or synthesis. The system 100 may include a base instrument 102 that is configured to receive and separably engage a removable cartridge 200 and/or a component with one or more reaction sites. The base instrument 102 and the removable cartridge 200 may be configured to interact with each other to transport a biological material to different locations within the system 100 and/or to conduct designated reactions that include the biological material in order to prepare the biological material for subsequent analysis (e.g., by synthesizing the biological material), and, optionally, to detect one or more events with the biological material. In some implementations, the base instrument 102 may be configured to detect one or more events with the biological material directly on the removable cartridge 200. The events may be indicative of a designated reaction with the biological material. The removable cartridge 200 may be constructed according to any of the cartridges described herein.

Although the following is with reference to the base instrument 102 and the removable cartridge 200 as shown in FIG. 1, it is understood that the base instrument 102 and the removable cartridge 200 illustrate only one implementation of the system 100 and that other implementations exist. For example, the base instrument 102 and the removable cartridge 200 include various components and features that, collectively, execute several operations for preparing the biological material and/or analyzing the biological material. Moreover, although the removable cartridge 200 described herein includes an element with the reaction sites, such as a flow cell having a plurality of wells, other cartridges may be independent of the element with the reaction sites and the element with the reaction sites may be separately insertable into the base instrument 102. That is, in some instances a flow cell may be removably inserted into the removable cartridge 200, which is then inserted into the base instrument 102. In some other implementations, the flow cell may be removably inserted directly into the base instrument 102 without the removable cartridge 200. In still further implementations, the flow cell may be integrated into the removable cartridge 200 that is inserted into the base instrument 102.

In the illustrated implementation, each of the base instrument 102 and the removable cartridge 200 are capable of performing certain functions. It is understood, however, that the base instrument 102 and the removable cartridge 200 may perform different functions and/or may share such functions. For example, the base instrument 102 is shown to include a detection assembly 110 (e.g., an imaging device) that is configured to detect the designated reactions at the removable cartridge 200. In alternative implementations, the removable cartridge 200 may include the detection assembly and may be communicatively coupled to one or more components of the base instrument 102. As another example, the base instrument 102 is a "dry" instrument that does not provide, receive, or exchange liquids with the removable cartridge 200. That is, as shown, the removable cartridge 200 includes a consumable reagent portion 210 and a flow cell receiving portion 220. The consumable reagent portion 210 may contain reagents used during biochemical analysis and/or synthesis. The flow cell receiving portion 220 may include an optically transparent region or other detectible region for the detection assembly 110 to perform detection of one or more events occurring within the flow cell receiving portion 220. In alternative implementations, the base instrument 102 may provide, for example, reagents or other liquids to the removable cartridge 200 that are subsequently consumed (e.g., used in designated reactions or synthesis procedures) by the removable cartridge 200.

As used herein, the biological material may include one or more biological or chemical substances, such as nucleosides, nucleotides, nucleic acids, polynucleotides, oligonucleotides, proteins, enzymes, peptides, oligopeptides, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological material may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, viruses including viral pathogens, liquids containing multi-celled organisms, biological swabs and biological washes. In some instances, the biological material may include a set of synthetic sequences, including but not limited to machine-written DNA, which may be fixed (e.g., attached in specific wells in a cartridge) or unfixed (e.g., stored in a tube).

In some implementations, the biological material may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological material. In other aspects, the added material may be a carrier for the biological material such as cell culture media or other buffered and/or pH adjusted and/or isotonic carrier that may allow for or preserve the biological function of the biological material.

It should be understood, however, that the biological material that is analyzed may be in a different form or state than the biological material loaded into or created by the system 100. For example, a biological material loaded into the system 100 may include whole blood or saliva or cell population that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological material" is used while describing a first operation, such as PCR, and used again while describing a subsequent second operation, such as sequencing, it is understood that the biological material in the second operation may be modified with respect to the biological material prior to or during the first operation. For example, sequencing (e.g. SBS) may be carried out on amplicon nucleic acids that are produced from template nucleic acids that are amplified in a prior amplification (e.g. PCR). In this case the amplicons are copies of the templates and the amplicons are present in higher quantity compared to the quantity of the templates.

In some implementations, the system 100 may automatically prepare a sample for biochemical analysis based on a substance provided by the user (e.g., whole blood or saliva or a population of cells). However, in other implementations, the system 100 may analyze biological materials that are partially or preliminarily prepared for analysis by the user. For example, the user may provide a solution including nucleic acids that were already isolated and/or amplified from whole blood, or may provide a virus sample in which the RNA or DNA sequence is partially or wholly exposed for processing.

As used herein, a "designated reaction" includes a change in at least one of a chemical, electrical, physical, or optical property (or quality) of an analyte-of-interest. In particular implementations, the designated reaction is an associative binding event (e.g., incorporation of a fluorescently labeled biomolecule with the analyte-of-interest). The designated reaction may be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Some reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction may also be addition or removal of a proton, for example, detectable as a change in pH of a surrounding solution or environment. An additional designated reaction may be detecting the flow of ions across a membrane (e.g., natural or synthetic bilayer membrane). For example, as ions flow through a membrane, the current is disrupted, and the disruption may be detected. Field sensing of charged tags may also be used as may thermal sensing and other suitable analytical sensing techniques.

In particular implementations, the designated reaction includes the incorporation of a fluorescently labeled molecule to an analyte. The analyte may be an oligonucleotide and the fluorescently labeled molecule may be a nucleotide. The designated reaction may be detected when an excitation light is directed toward the oligonucleotide having the labeled nucleotide, and the fluorophore emits a detectable fluorescent signal. In alternative implementations, the detected fluorescence is a result of chemiluminescence and/or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological material is immobilized. The reaction components may interact directly or indirectly with the biological material. In some implementations, the removable cartridge 200 is preloaded with one or more of the reaction components involved in carrying out a designated assay protocol. Preloading may occur at one location (e.g. a manufacturing facility) prior to receipt of the cartridge 200 by a user (e.g. at a customer's facility). For example, the one or more reaction components or reagents may be preloaded into the consumable reagent portion 210. In some implementations, the removable cartridge 200 may also be preloaded with a flow cell in the flow cell receiving portion 220.

In some implementations, the base instrument 102 may be configured to interact with one removable cartridge 200 per session. After the session, the removable cartridge 200 may be replaced with another removable cartridge 200. In other implementations, the base instrument 102 may be configured to interact with more than one removable cartridge 200 per session. As used herein, the term "session" includes performing at least one of sample preparation and/or biochemical analysis protocol. Sample preparation may include synthesizing the biological material; and/or separating, isolating, modifying, and/or amplifying one or more components of the biological material so that the prepared biological material is suitable for analysis. In some implementations, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 200 and the base instrument 102 may include the components for executing the different operations. The operations of an assay protocol may include fluidic operations, thermal-control operations, detection operations, and/or mechanical operations.

A fluidic operation includes controlling the flow of fluid (e.g., liquid or gas) through the system 100, which may be actuated by the base instrument 102 and/or by the removable cartridge 200. In one example, the fluid is in liquid form. For example, a fluidic operation may include controlling a pump to induce flow of the biological material or a reaction component into a reaction chamber.

A thermal-control operation may include controlling a temperature of a designated portion of the system 100, such as one or more portions of the removable cartridge 200. By way of example, a thermal-control operation may include raising or lowering a temperature of a polymerase chain reaction (PCR) zone where a liquid that includes the biological material is stored.

A detection operation may include controlling activation of a detector or monitoring activity of the detector to detect predetermined properties, qualities, or characteristics of the biological material. As one example, the detection operation may include capturing images of a designated area that includes the biological material to detect fluorescent emissions from the designated area. The detection operation may include controlling a light source to illuminate the biological material or controlling a detector to observe the biological material.

A mechanical operation may include controlling a movement or position of a designated component. For example, a mechanical operation may include controlling a motor to move a valve-control component in the base instrument 102 that operably engages a movable valve in the removable cartridge 200. In some cases, a combination of different operations may occur concurrently. For example, the detector may capture images of the reaction chamber as the pump controls the flow of fluid through the reaction chamber. In some cases, different operations directed toward different biological materials may occur concurrently. For instance, a first biological material may be undergoing amplification (e.g., PCR) while a second biological material may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous-based and include polar molecules exhibiting surface tension that holds the liquid together. A liquid may also include non-polar molecules, such as in an oil-based or non-aqueous substance. It is understood that references to a liquid in the present application may include a liquid comprising the combination of two or more liquids. For example, separate reagent solutions may be later combined to conduct designated reactions.

One or more implementations may include retaining the biological material (e.g., template nucleic acid) at a designated location where the biological material is analyzed. As used herein, the term "retained," when used with respect to a biological material, includes attaching the biological material to a surface or confining the biological material within a designated space. As used herein, the term "immobilized," when used with respect to a biological material, includes attaching the biological material to a surface in or on a solid support. Immobilization may include attaching the biological material at a molecular level to the surface. For example, a biological material may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological material to the surface. Immobilizing a biological material to a surface of a substrate may be based upon the properties of the surface of the substrate, the liquid medium carrying the biological material, and the properties of the biological material itself. In some cases, a substrate surface may be functionalized (e.g., chemically or physically modified) to facilitate immobilizing the biological material to the substrate surface. The substrate surface may be first modified to have functional groups bound to the surface. The functional groups may then bind to the biological material to immobilize the biological material thereon. In some cases, a biological material may be immobilized to a surface via a gel.

In some implementations, nucleic acids may be immobilized to a surface and amplified using bridge amplification. Another useful method for amplifying nucleic acids on a surface is rolling circle amplification (RCA), for example, using methods set forth in further detail below. In some implementations, the nucleic acids may be attached to a surface and amplified using one or more primer pairs. For example, one of the primers may be in solution and the other primer may be immobilized on the surface (e.g., 5'-attached). By way of example, a nucleic acid molecule may hybridize to one of the primers on the surface followed by extension of the immobilized primer to produce a first copy of the nucleic acid. The primer in solution then hybridizes to the first copy of the nucleic acid which may be extended using the first copy of the nucleic acid as a template. Optionally, after the first copy of the nucleic acid is produced, the original nucleic acid molecule may hybridize to a second immobilized primer on the surface and may be extended at the same time or after the primer in solution is extended. In any implementation, repeated rounds of extension (e.g., amplification) using the immobilized primer and primer in solution may be used to provide multiple copies of the nucleic acid. In some implementations, the biological material may be confined within a predetermined space with reaction components that are configured to be used during amplification of the biological material (e.g., PCR).

One or more implementations set forth herein may be configured to execute an assay protocol that is or includes an amplification (e.g., PCR) protocol. During the amplification protocol, a temperature of the biological material within a reservoir or channel may be changed in order to amplify a target sequence or the biological material (e.g., DNA of the biological material). By way of example, the biological material may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Implementations may execute multiple amplification cycles. It is noted that the above cycle describes only one particular implementation and that alternative implementations may include modifications to the amplification protocol.

The methods and systems set forth herein may use arrays having features at any of a variety of densities including, for example, at least about 10 features/cm$^2$, about 100 features/cm$^2$, about 500 features/cm$^2$, about 1,000 features/cm$^2$, about 5,000 features/cm$^2$, about 10,000 features/cm$^2$, about 50,000 features/cm$^2$, about 100,000 features/cm$^2$, about 1,000,000 features/cm$^2$, about 5,000,000 features/cm$^2$, or higher. The methods and apparatus set forth herein may include detection components or devices having a resolution that is at least sufficient to resolve individual features at one or more of these densities.

The base instrument 102 may include a user interface 130 that is configured to receive user inputs for conducting a designated assay protocol and/or configured to communicate information to the user regarding the assay. The user interface 130 may be incorporated with the base instrument 102. For example, the user interface 130 may include a touchscreen that is attached to a housing of the base instrument 102 and configured to identify a touch from the user and a location of the touch relative to information displayed on the touchscreen. Alternatively, the user interface 130 may be located remotely with respect to the base instrument 102.

II. Cartridge

The removable cartridge 200 is configured to separably engage or removably couple to the base instrument 102 at a cartridge chamber 140. As used herein, when the terms "separably engaged" or "removably coupled" (or the like) are used to describe a relationship between a removable cartridge 200 and a base instrument 102. The term is intended to mean that a connection between the removable cartridge 200 and the base instrument 102 are separable without destroying the base instrument 102. Accordingly, the removable cartridge 200 may be separably engaged to the base instrument 102 in an electrical manner such that the electrical contacts of the base instrument 102 are not destroyed. The removable cartridge 200 may be separably engaged to the base instrument 102 in a mechanical manner such that features of the base instrument 102 that hold the removable cartridge 200, such as the cartridge chamber 140, are not destroyed. The removable cartridge 200 may be separably engaged to the base instrument 102 in a fluidic manner such that the ports of the base instrument 102 are not destroyed. The base instrument 102 is not considered to be "destroyed," for example, if only a simple adjustment to the component (e.g., realigning) or a simple replacement (e.g., replacing a nozzle) is required. Components (e.g., the removable cartridge 200 and the base instrument 102) may be readily separable when the components may be separated from each other without undue effort or a significant amount of time spent in separating the components. In some implementations, the removable cartridge 200 and the base instrument 102 may be readily separable without destroying either the removable cartridge 200 or the base instrument 102.

In some implementations, the removable cartridge 200 may be permanently modified or partially damaged during a session with the base instrument 102. For instance, containers holding liquids may include foil covers that are pierced to permit the liquid to flow through the system 100. In such implementations, the foil covers may be damaged such that the damaged container is to be replaced with another container. In particular implementations, the removable cartridge 200 is a disposable cartridge such that the removable cartridge 200 may be replaced and optionally disposed after a single use. Similarly, a flow cell of the removable cartridge 200 may be separately disposable such that the flow cell may be replaced and optionally disposed after a single use.

In other implementations, the removable cartridge 200 may be used for more than one session while engaged with the base instrument 102 and/or may be removed from the base instrument 102, reloaded with reagents, and re-engaged to the base instrument 102 to conduct additional designated reactions. Accordingly, the removable cartridge 200 may be refurbished in some cases such that the same removable cartridge 200 may be used with different consumables (e.g., reaction components and biological materials). Refurbishing may be carried out at a manufacturing facility after the cartridge 200 has been removed from a base instrument 102 located at a customer's facility.

The cartridge chamber 140 may include a slot, mount, connector interface, and/or any other feature to receive the removable cartridge 200 or a portion thereof to interact with the base instrument 102.

The removable cartridge 200 may include a fluidic network that may hold and direct fluids (e.g., liquids or gases) therethrough. The fluidic network may include a plurality of interconnected fluidic elements that are capable of storing a fluid and/or permitting a fluid to flow therethrough. Non-limiting examples of fluidic elements include channels, ports of the channels, cavities, storage devices, reservoirs of the storage devices, reaction chambers, waste reservoirs, detection chambers, multipurpose chambers for reaction and detection, and the like. For example, the consumable reagent portion 210 may include one or more reagent wells or chambers storing reagents and may be part of or coupled to the fluidic network. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some implementations, it may not be possible to direct the fluid in the channel back to the assay reservoir. In particular implementations, the fluidic network may be configured to receive a biological material and direct the biological material through sample preparation and/or sample analysis. The fluidic network may direct the biological material and other reaction components to a waste reservoir.

Figure 2:
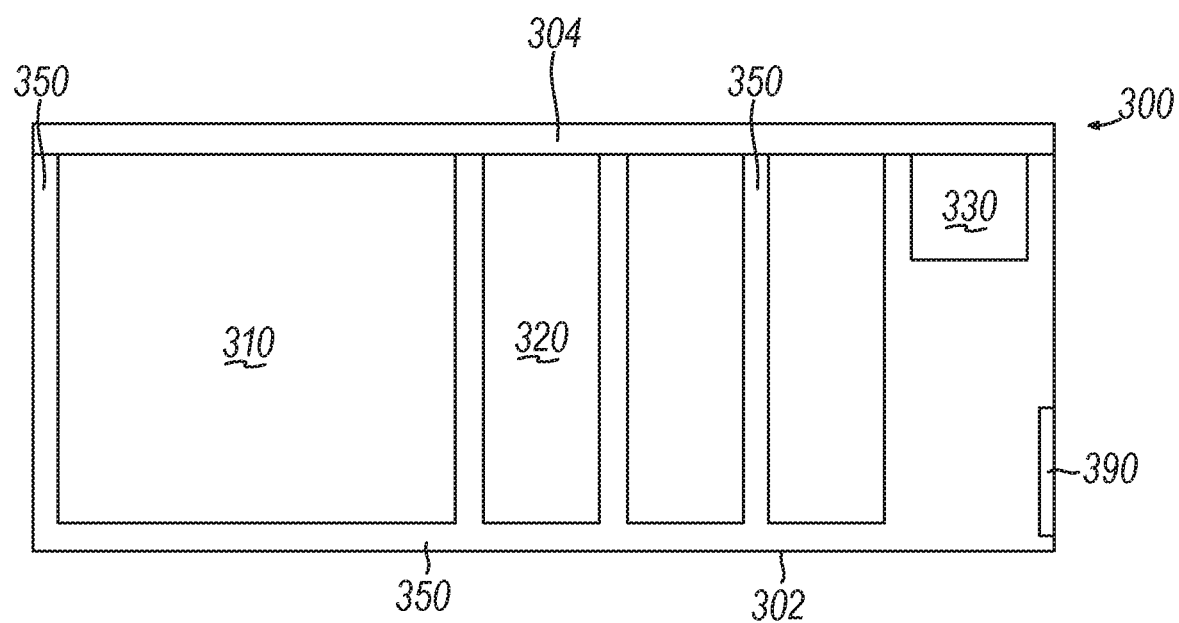
FIG. 2 depicts a block schematic cross-sectional view of an example of a consumable cartridge that may be utilized with the system of FIG. 1.

FIG. 2 depicts an implementation of a consumable cartridge 300. The consumable cartridge may be part of a combined removable cartridge, such as consumable reagent portion 210 of removable cartridge 200 of FIG. 1; or may be a separate reagent cartridge. The consumable cartridge 300 may include a housing 302 and a top 304. The housing 302 may comprise a non-conductive polymer or other material and be formed to make one or more reagent chambers 310, 320, 330. The reagent chambers 310, 320, 330 may be varying in size to accommodate varying volumes of reagents to be stored therein. For instance, a first chamber 310 may be larger than a second chamber 320, and the second chamber 320 may be larger than a third chamber 330. The first chamber 310 is sized to accommodate a larger volume of a particular reagent, such as a buffer reagent. The second chamber 320 may be sized to accommodate a smaller volume of reagent than the first chamber 310, such as a reagent chamber holding a cleaving reagent. The third chamber 330 may be sized to accommodate an even smaller volume of reagent than the first chamber 310 and the second chamber 320, such as a reagent chamber holding a fully functional nucleotide containing reagent.

In the illustrated implementation, the housing 302 has a plurality of housing walls or sides 350 forming the chambers 310, 320, 330 therein. In the illustrated implementation, the housing 302 forms a structure that is at least substantially unitary or monolithic. In alternative implementations, the housing 302 may be constructed by one or more subcomponents that are combined to form the housing 302, such as independently formed compartments for chambers 310, 320, and 330.

The housing 302 may be sealed by the top 304 once reagents are provided into the respective chambers 310, 320, 330. The top 304 may comprise a conductive or non-conductive material. For instance, the top 304 may be an aluminum foil seal that is adhesively coupled to top surfaces of the housing 302 to seal the reagents within their respective chambers 310, 320, 330. In other implementations, the top 304 may be a plastic seal that is adhesively coupled to top surfaces of the housing 302 to seal the reagents within their respective chambers 310, 320, 330.

In some implementations, the housing 302 may also include an identifier 390. The identifier 390 may be a radio-frequency identification (RFID) transponder, a barcode, an identification chip, and/or other identifier. In some implementations, the identifier 390 may be embedded in the housing 302 or attached to an exterior surface. The identifier 390 may include data for a unique identifier for the consumable cartridge 300 and/or data for a type of the consumable cartridge 300. The data of the identifier 390 may be read by the base instrument 102 or a separate device configured for warming the consumable cartridge 300, as described herein.

In some implementations, the consumable cartridge 300 may include other components, such as valves, pumps, fluidic lines, ports, etc. In some implementations, the consumable cartridge 300 may be contained within a further exterior housing.

III. System Controller

The base instrument 102 may also include a system controller 120 that is configured to control operation of at least one of the removable cartridge 200 and/or the detection assembly 110. The system controller 120 may be implemented utilizing any combination of dedicated hardware circuitry, boards, DSPs, processors, etc. Alternatively, the system controller 120 may be implemented utilizing an off-the-shelf PC with a single processor or multiple processors, with the functional operations distributed between the processors. As a further option, the system controller 120 may be implemented utilizing a hybrid configuration in which certain modular functions are performed utilizing dedicated hardware, while the remaining modular functions are performed utilizing an off-the-shelf PC and the like.

The system controller 120 may include a plurality of circuitry modules that are configured to control operation of certain components of the base instrument 102 and/or the removable cartridge 200. The term "module" herein may refer to a hardware device configured to perform specific task(s). For instance, the circuitry modules may include a flow-control module that is configured to control flow of fluids through the fluidic network of the removable cartridge 200. The flow-control module may be operably coupled to valve actuators and/or s system pump. The flow-control module may selectively activate the valve actuators and/or the system pump to induce flow of fluid through one or more paths and/or to block flow of fluid through one or more paths.

The system controller 120 may also include a thermal-control module. The thermal-control module may control a thermocycler or other thermal component to provide and/or remove thermal energy from a sample-preparation region of the removable cartridge 200 and/or any other region of the removeable cartridge 200. In one particular example, a thermocycler may increase and/or decrease a temperature that is experienced by the biological material in accordance with a PCR protocol.

The system controller 120 may also include a detection module that is configured to control the detection assembly 110 to obtain data regarding the biological material. The detection module may control operation of the detection assembly 110 either through a direct wired connection or through the contact array if the detection assembly 110 is part of the removable cartridge 200. The detection module may control the detection assembly 110 to obtain data at predetermined times or for predetermined time periods. By way of example, the detection module may control the detection assembly 110 to capture an image of a reaction chamber of the flow cell receiving portion 220 of the removable cartridge when the biological material has a fluorophore attached thereto. In some implementations, a plurality of images may be obtained.

Optionally, the system controller 120 may include an analysis module that is configured to analyze the data to provide at least partial results to a user of the system 100. For example, the analysis module may analyze the imaging data provided by the detection assembly 110. The analysis may include identifying a sequence of nucleic acids of the biological material.

The system controller 120 and/or the circuitry modules described above may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an implementation, the system controller 120 and/or the circuitry modules execute a set of instructions that are stored in a computer- or machine-readable medium therein in order to perform one or more assay protocols and/or other operations. The set of instructions may be stored in the form of information sources or physical memory elements within the base instrument 102 and/or the removable cartridge 200. The protocols performed by the system 100 may be used to carry out, for example, machine-writing DNA or otherwise synthesizing DNA (e.g., converting binary data into a DNA sequence and then synthesizing DNA strands or other polynucleotides representing the binary data), quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various implementations described herein. The set of instructions may be in the form of a software program. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are only examples and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 120 may be connected to the other components or sub-systems of the system 100 via communication links, which may be hardwired or wireless. The system controller 120 may also be communicatively connected to off-site systems or servers. The system controller 120 may receive user inputs or commands, from a user interface 130. The user interface 130 may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the system 100 at different locations. In some implementations, one or more components may be integrated with the base instrument 102 and one or more components may be located remotely with respect to the base instrument 102.

IV. Flow Cell

Figure 3:
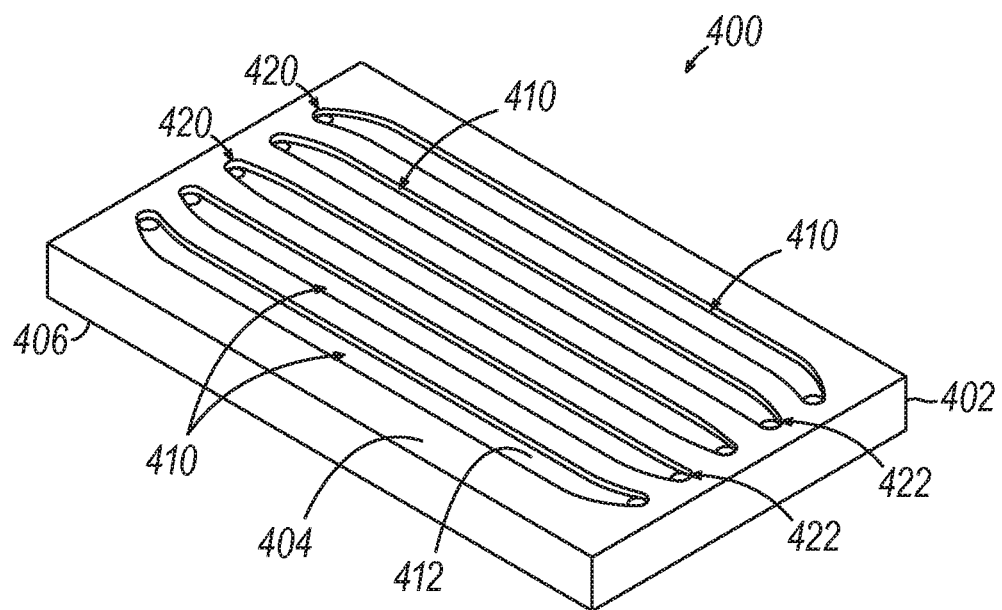
FIG. 3 depicts a perspective view of an example of a flow cell that may be utilized with the system of FIG. 1.
Figure 4:
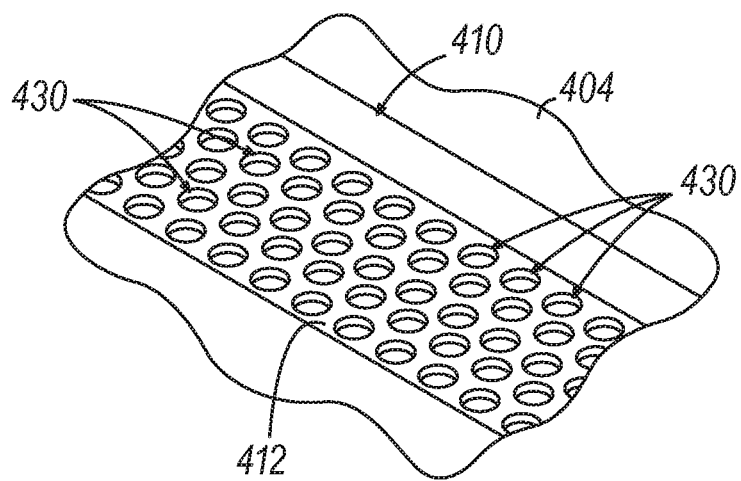
FIG. 4 depicts an enlarged perspective view of a channel of the flow cell of FIG. 3.

FIGS. 3-4 depict an example of a flow cell 400 that may be used with system 100. Flow cell of this example includes a body defining a plurality of elongate flow channels 410, which are recessed below an upper surface 404 of the body 402. The flow channels 410 are generally parallel with each other and extend along substantially the entire length of body 402. While five flow channels 410 are shown, a flow cell 400 may include any other suitable number of flow channels 410, including more or fewer than five flow channels 410. The flow cell 400 of this example also includes a set of inlet ports 420 and a set of outlet ports 422, with each port 420, 422 being associated with a corresponding flow channel 410. Thus, each inlet port 420 may be utilized to communicate fluids (e.g., reagents, etc.) to the corresponding channel 410; while each outlet port 422 may be utilized to communicate fluids from the corresponding flow channel 410.

In some versions, the flow cell 400 is directly integrated into the flow cell receiving portion 220 of the removable cartridge 200. In some other versions, the flow cell 400 is removably coupled with the flow cell receiving portion 220 of the removable cartridge 200. In versions where the flow cell 400 is either directly integrated into the flow cell receiving portion 220 or removably coupled with the flow cell receiving portion 220, the flow channels 410 of the flow cell 400 may receive fluids from the consumable reagent portion 210 via the inlet ports 420, which may be fluidly coupled with reagents stored in the consumable reagent portion 210. Of course, the flow channels 410 may be coupled with various other fluid sources or reservoirs, etc., via the ports 420, 422. As another illustrative variation, some versions of consumable cartridge 300 may be configured to removably receive or otherwise integrate the flow cell 400. In such versions, the flow channels 410 of the flow cell 400 may receive fluids from the reagent chambers 310, 320, 330 via the inlet ports 420. Other suitable ways in which the flow cell 400 may be incorporated into the system 100 will be apparent to those skilled in the art in view of the teachings herein.

FIG. 4 shows a flow channel 410 of the flow cell 400 in greater detail. As shown, the flow channel 410 includes a plurality of wells 430 formed in a base surface 412 of the flow channel 410. As will be described in greater detail below each well 430 is configured to contain DNA strands or other polynucleotides, such as machine-written polynucleotides. In some versions, each well 430 has a cylindraceous configuration, with a generally circular cross-sectional profile. In some other versions, each well 430 has a polygonal (e.g., hexagonal, octagonal, etc.) cross-sectional profile. Alternatively, wells 430 may have any other suitable configuration. It should also be understood that wells 430 may be arranged in any suitable pattern, including but not limited to a grid pattern.

Figure 5:
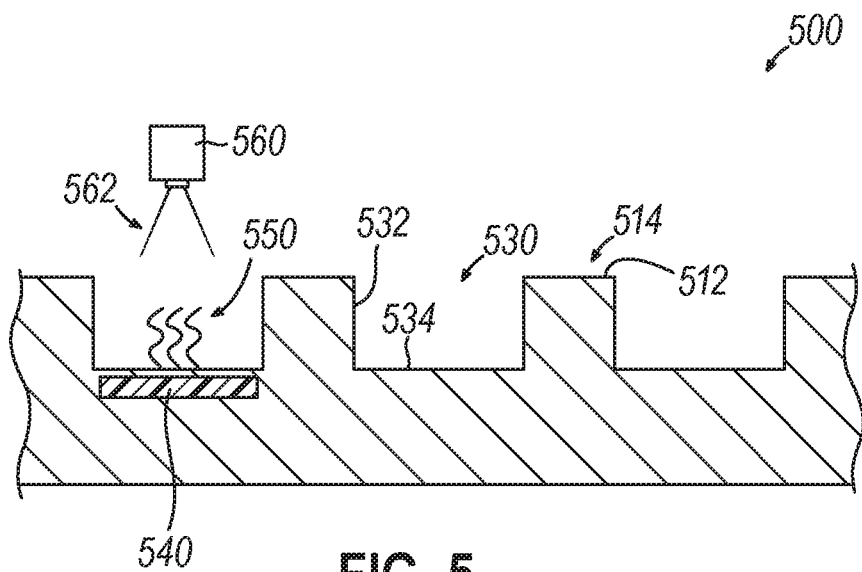
FIG. 5 depicts a block schematic cross-sectional view of an example of wells that may be incorporated into the channel of FIG. 4.

FIG. 5 shows a portion of a channel within a flow cell 500 that is an example of a variation of the flow cell 400. In other words, the channel depicted in FIG. 5 is a variation of the flow channel 410 of the flow cell 400. This flow cell 500 is operable to read polynucleotide strands 550 that are secured to the floor 534 of wells 530 in the flow cell 500. By way of example only, the floor 534 where polynucleotide strands 550 are secured may include a co-block polymer capped with azido. By way of further example only, such a polymer may comprise a poly(N-(5-azidoacetamidylpentyl)acrylamide-co-acrylamide) (PAZAM) coating provided in accordance with at least some of the teachings of U.S. Pat. No. 9,012,022, entitled "Polymer Coatings," issued Apr. 21, 2015, which is incorporated by reference herein in its entirety. Such a polymer may be incorporated into any of the various flow cells described herein.

In the present example, the wells 530 are separated by interstitial spaces 514 provided by the base surface 512 of the flow cell 500. Each well 530 has a sidewall 532 and a floor 534. The flow cell 500 in this example is operable to provide an image sensor 540 under each well 530. In some versions, each well 530 has at least one corresponding image sensor 540, with the image sensors 540 being fixed in position relative to the wells 530. Each image sensor 540 may comprise a CMOS image sensor, a CCD image sensor, or any other suitable kind of image sensor. By way of example only, each well 530 may have one associated image sensor 540 or a plurality of associated image sensors 540. As another variation, a single image sensor 540 may be associated with two or more wells 530. In some versions, one or more image sensors 540 move relative to the wells 530, such that a single image sensor 540 or single group of image sensors 540 may be moved relative to the wells 530. As yet another variation, the flow cell 500 may be movable in relation to the single image sensor 540 or single group of image sensors 540, which may be at least substantially fixed in position.

Each image sensor 540 may be directly incorporated into the flow cell 500. Alternatively, each image sensor 540 may be directly incorporated into a cartridge such as the removable cartridge 200, with the flow cell 500 being integrated into or otherwise coupled with the cartridge. As yet another illustrative variation, each image sensor 540 may be directly incorporated into the base instrument 102 (e.g., as part of the detection assembly 110 noted above). Regardless of where the image sensor(s) 540 is/are located, the image sensor(s) 540 may be integrated into a printed circuit that includes other components (e.g., control circuitry, etc.). In versions where the one or more image sensors 540 are not directly incorporated into the flow cell 500, the flow cell 500 may include optically transmissive features (e.g., windows, etc.) that allow the one or more image sensors 540 to capture fluorescence emitted by the one or more fluorophores associated with the polynucleotide strands 550 that are secured to the floors 534 of the wells 530 in the flow cell 500 as described in greater detail below. It should also be understood that various kinds of optical elements (e.g., lenses, optical waveguides, etc.) may be interposed between the floors 534 of the wells 530 and the corresponding image sensor(s) 540.

As also shown in FIG. 5, a light source 560 is operable to project light 562 into the well 530. In some versions, each well 530 has at least one corresponding light source 560, with the light sources 560 being fixed in position relative to the wells 530. By way of example only, each well 530 may have one associated light source 560 or a plurality of associated light sources 560. As another variation, a single light source 560 may be associated with two or more wells 530. In some other versions, one or more light sources 560 move relative to the wells 530, such that a single light source 560 or single group of light sources 560 may be moved relative to the wells 530. As yet another variation, the flow cell 500 may be movable in relation to the single light source 560 or single group of light sources 560, which may be substantially fixed in position. By way of example only, each light source 560 may include one or more lasers. In another example, the light source 560 may include one or more diodes.

Each light source 560 may be directly incorporated into the flow cell 500. Alternatively, each light source 560 may be directly incorporated into a cartridge such as the removable cartridge 200, with the flow cell 500 being integrated into or otherwise coupled with the cartridge. As yet another illustrative variation, each light source 560 may be directly incorporated into the base instrument 102 (e.g., as part of the detection assembly 110 noted above). In versions where the one or more light sources 560 are not directly incorporated into the flow cell 500, the flow cell 500 may include optically transmissive features (e.g., windows, etc.) that allow the wells 530 to receive the light emitted by the one or more light source 560, to thereby enable the light to reach the polynucleotide strands 550 that are secured to the floor 534 of the wells 530. It should also be understood that various kinds of optical elements (e.g., lenses, optical waveguides, etc.) may be interposed between the wells 530 and the corresponding light source(s) 560.

Figure 6:
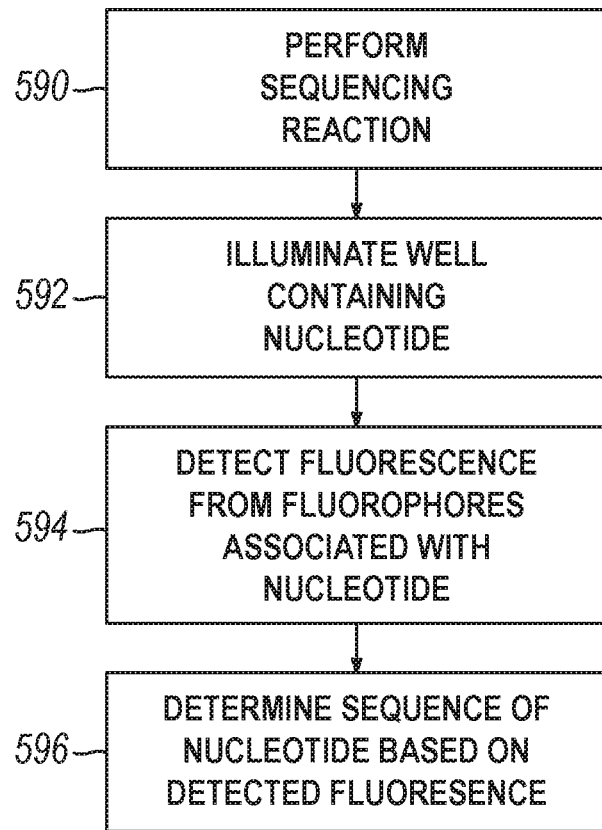
FIG. 6 depicts a flow chart of an example of a process for reading polynucleotides.

As described elsewhere herein and as is shown in block 590 of FIG. 6, a DNA reading process may begin with performing a sequencing reaction in the targeted well(s) 530 (e.g., in accordance with at least some of the teachings of U.S. Pat. No. 9,453,258, entitled "Methods and Compositions for Nucleic Acid Sequencing," issued Sep. 27, 2016, which is incorporated by reference herein in its entirety). Next, as shown in block 592 of FIG. 6, the light source(s) 560 is/are activated over the targeted well(s) 530 to thereby illuminate the targeted well(s) 530. The projected light 562 may cause a fluorophore associated with the polynucleotide strands 550 to fluoresce. Accordingly, as shown in block 594 of FIG. 6, the corresponding image sensor(s) 540 may detect the fluorescence emitted from the one or more fluorophores associated with the polynucleotide strands 550. The system controller 120 of the base instrument 102 may drive the light source(s) 560 to emit the light. The system controller 120 of the base instrument 102 may also process the image data obtained from the image sensor(s) 540, representing the fluorescent emission profiles from the polynucleotide strands 550 in the wells 530. Using this image data from the image sensor(s) 540, and as shown in block 596 of FIG. 6, the system controller 120 may determine the sequence of bases in each polynucleotide strand 550. By way of example only, this process and equipment may be utilized to map a genome or otherwise determine biological information associated with a naturally occurring organism, where DNA strands or other polynucleotides are obtained from or otherwise based on a naturally occurring organism. Alternatively, the above-described process and equipment may be utilized to obtain data stored in machine-written DNA as will be described in greater detail below.

By way of further example only, when carrying out the above-described procedure shown in FIG. 6, time space sequencing reactions may utilize one or more chemistries and imaging events or steps to differentiate between a plurality of analytes (e.g., four nucleotides) that are incorporated into a growing nucleic acid strand during a sequencing reaction; or alternatively, fewer than four different colors may be detected in a mixture having four different nucleotides while still resulting in the determination of the four different nucleotides (e.g., in a sequencing reaction). A pair of nucleotide types may be detected at the same wavelength, but distinguished based on a difference in intensity for one member of the pair compared to the other, or based on a change to one member of the pair (e.g., via chemical modification, photochemical modification, or physical modification) that causes apparent signal to appear or disappear compared to the signal detected for the other member of the pair.

V. Machine-Writing Biological Material

In some implementations, a system 100 such as the system 100 shown in FIG. 1 may be configured to synthesize biological materials (e.g. polynucleotide, such as DNA) to encode data that may later be retrieved through the performance of assays such as those described above. In some implementations, this type of encoding may be performed by assigning values to nucleotide bases (e.g., binary values, such as 0 or 1, ternary values such as 0, 1 or 2, etc.), converting the data to be encoded into a string of the relevant values (e.g., converting a textual message into a binary string using the ASCII encoding scheme), and then creating one or more polynucleotides made up of nucleotides having bases in a sequence corresponding to the string obtained by converting the data.

Figure 7:
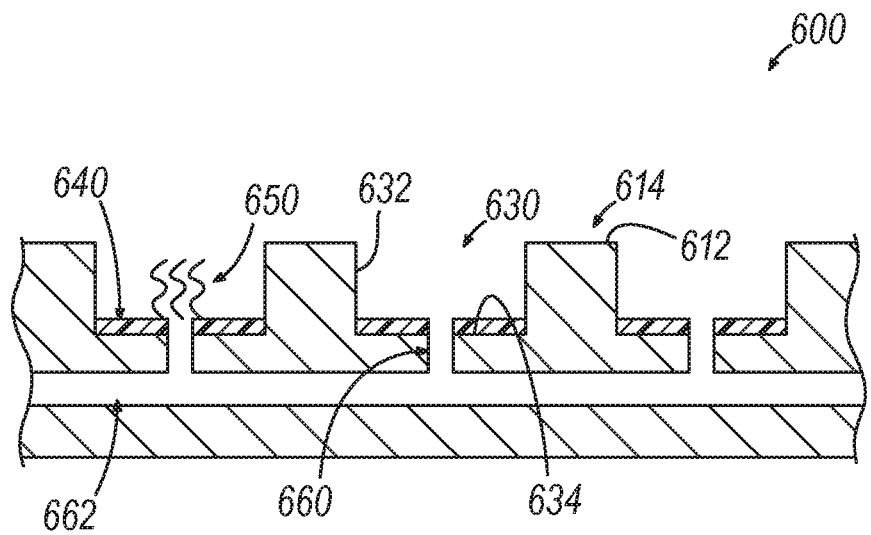
FIG. 7 depicts a block schematic cross-sectional view of another example of wells that may be incorporated into the channel of FIG. 4.

In some implementations, the creation of such polynucleotides may be performed using a version of the flow cell 400 having an array of wells 630 that are configured as shown in FIG. 7. FIG. 7 shows a portion of a channel within a flow cell 600 that is an example of a variation of the flow cell 400. In other words, the channel depicted in FIG. 7 is a variation of the flow channel 410 of the flow cell 400. In this example, each well 630 is recessed below a base surface 612 of the flow cell 600. The wells 630 are thus spaced apart from each other by interstitial spaces 614. By way of example only, the wells 630 may be arranged in a grid or any other suitable pattern along the base surface 612 of the flow cell 600. Each well 630 of this example includes a sidewall 632 and a floor 634. Each well 630 of this example further includes a respective electrode assembly 640 positioned on the floor 634 of the well 630. In some versions, each electrode assembly 640 includes just a single electrode element. In some other versions, each electrode assembly 640 includes a plurality of electrode elements or segments. The terms "electrode" and "electrode assembly" should be read herein as being interchangeable.

Base instrument 102 is operable to independently activate electrode assemblies 640, such that one or more electrode assemblies 640 may be in an activated state while one or more other electrode assemblies 640 are not in an activated state. In some versions, a CMOS device or other device is used to control electrode assemblies 640. Such a CMOS device may be integrated directly into the flow cell 600, may be integrated into a cartridge (e.g., cartridge 200) in which the flow cell 600 is incorporated, or may be integrated directly into the base instrument 102. As shown in FIG. 7, each electrode assembly 640 extends along the full width of floor 634, terminating at the sidewall 632 of the corresponding well 630. In other versions, each electrode assembly 640 may extend along only a portion of the floor 634. For instance, some versions of electrode assembly 640 may terminate interiorly relative to the sidewall 632. While each electrode assembly 540 is schematically depicted as a single element in FIG. 5, it should be understood that each electrode assembly 540 may in fact be formed by a plurality of discrete electrodes rather than just consisting of one single electrode.

As shown in FIG. 7, specific polynucleotide strands 650 may be created in individual wells 630 by activating the electrode assembly 640 of the relevant wells 630 to electrochemically generate acid that may deprotect the end group of the polynucleotide strand 650 in the well 630. By way of example only, polynucleotide strands 650 may be chemically attached to the surface at the bottom of the well 630 using linkers having chemistries such as silane chemistry on one end and DNA synthesis compatible chemistry (e.g., a short oligo for enzyme to bind to) on the other end.

To facilitate reagent exchange (e.g., transmission of a deblocking agent), each electrode assembly 640 and the floor 634 of each well 630 may include at least one opening 660 in this example. The openings 660 may be fluidly coupled with a flow channel 662 that extends underneath the wells 630, below the floors 634. To provide such an opening 660 through the electrode assembly 640, the electrode assembly 640 may be annular in shape, may be placed in quadrants, may be placed on the perimeter or sidewall 632 of the well 630, or may be placed or shaped in other suitable manners to avoid interference with reagent exchange and/or passage of light (e.g., as may be used in a sequencing process that involved detection of fluorescent emissions). In other implementations, reagents may be provided into the flow channel of the flow cell 600 without the openings 660. It should be understood that the openings 660 may be optional and may be omitted in some versions. Similarly, the flow channel 662 may be optional and may be omitted in some versions.

Figure 9:
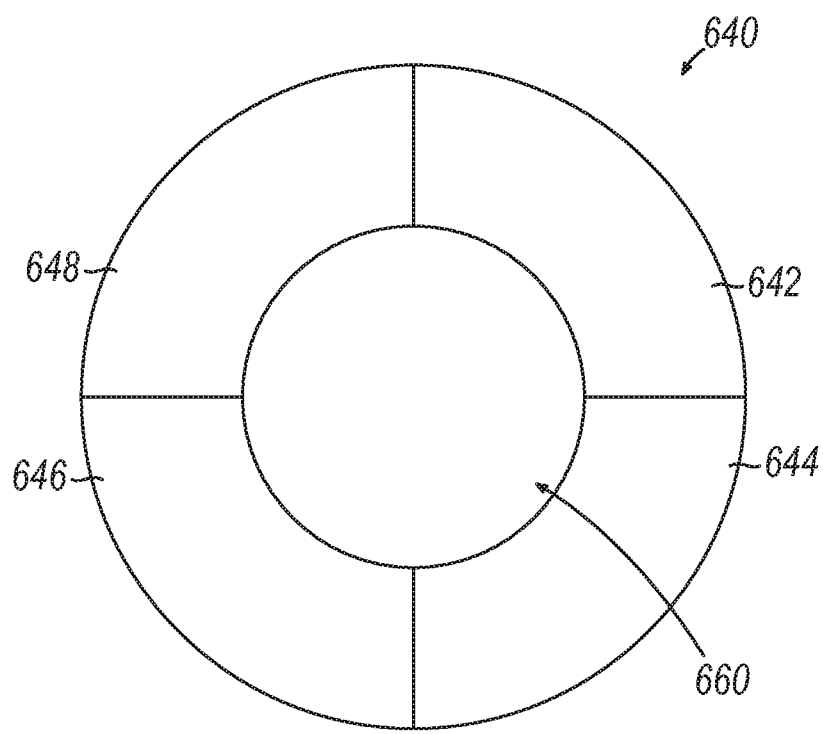
FIG. 9 depicts a top plan view of an example of an electrode assembly.

FIG. 9 shows an example of a form that electrode assembly 640 may take. In this example, electrode assembly 640 includes four discrete electrode segments 642, 644, 646, 648 that together define an annular shape. The electrode segments 642, 644, 646, 648 are thus configured as discrete yet adjacent quadrants of a ring. Each electrode segment 642, 644, 646, 648 may be configured to provide a predetermined charge that is uniquely associated with a particular nucleotide. For instance, electrode segment 642 may be configured to provide a charge that is uniquely associated with adenine; electrode segment 644 may be configured to provide a charge that is uniquely associated with cytosine; electrode segment 646 may be configured to provide a charge that is uniquely associated with guanine; and electrode segment 648 may be configured to provide a charge that is uniquely associated with thymine. When a mixture of those four nucleotides are flowed through the flow channel above the wells 630, activation of electrode segments 642, 644, 646, 648 may cause the corresponding nucleotides from that flow to adhere to the strand 650. Thus, when electrode segment 642 is activated, it may effect writing of adenine to the strand 650; when electrode segment 644 is activated, it may effect writing of cytosine to the strand 650; when electrode segment 646 is activated, it may effect writing of guanine to the strand 650; and when electrode segment 648 is activated, it may effect writing of thymine to the strand 650. This writing may be provided by the activated electrode segment 642, 644, 646, 648 hybridizing the inhibitor of the enzyme for the pixel associated with the activated electrode segment 642, 644, 646, 648. While electrode segments 642, 644, 646, 648 are shown as forming an annular shape in FIG. 9, it should be understood that any other suitable shape or shapes may be formed by electrode segments 642, 644, 646, 648. In still other implementations, a single electrode may be utilized for the electrode assembly 640 and the charge may be modulated to incorporate various nucleotides to be written to the DNA strand or other polynucleotide.

As another example, the electrode assembly 640 may be activated to provide a localized (e.g., localized within the well 630 in which the electrode assembly 640 is disposed), electrochemically generated change in pH; and/or electrochemically generate a moiety (e.g., a reducing or oxidizing reagent) locally to remove a block from a nucleotide. As yet another variation, different nucleotides may have different blocks; and those blocks may be photocleaved based on a wavelength of light communicated to the well 630 (e.g., light 562 projected from the light source 560). As still another variation, different nucleotides may have different blocks; and those blocks may be cleaved based on certain other conditions. For instance, one of the four blocks may be removed based on a combination of a reducing condition plus either high local pH or low local pH; another of the four blocks may be removed based on a combination of an oxidative condition plus either high local pH or low local pH; another of the four blocks may be removed based on a combination of light and a high local pH; and another of the four blocks may be removed based on a combination of light and a low local pH. Thus, four nucleotides may be incorporated at the same time, but with selective unblocking occurring in response to four different sets of conditions.

The electrode assembly 640 further defines the opening 660 at the center of the arrangement of the electrode segments 642, 644, 646, 648. As noted above, this opening 660 may provide a path for fluid communication between the flow channel 662 and the wells 630, thereby allowing reagents, etc. that are flowed through the flow channel 662 to reach the wells 630. As also noted above, some variations may omit the flow channel 662 and provide communication of reagents, etc. to the wells 630 in some other fashion (e.g., through passive diffusion, etc.). Regardless of whether fluid is communicated through the opening 660, the opening 660 may provide a path for optical transmission through the bottom of the well 630 during a read cycle, as described herein. In some versions, the opening 660 may be optional and may thus be omitted. In versions where the opening 660 is omitted, fluids may be communicated to the wells 630 via one or more flow channels that are above the wells 630 or otherwise positioned in relation to the wells 630. Moreover, the opening 660 may not be needed for providing a path for optical transmission through the bottom of the well 630 during a read cycle. For instance, as described below in relation to the flow cell 601, the electrode assembly 640 may comprise an optically transparent material (e.g., optically transparent conducting film (TCF), etc.), and the flow cell 600 itself may comprise an optically transparent material (e.g., glass), such that the electrode assembly 640 and the material forming the flow cell 600 may allow the fluorescence emitted from the one or more fluorophores associated with the machine-written polynucleotide strands 650 to reach an image sensor 540 that is under the well 630.

Figure 8:
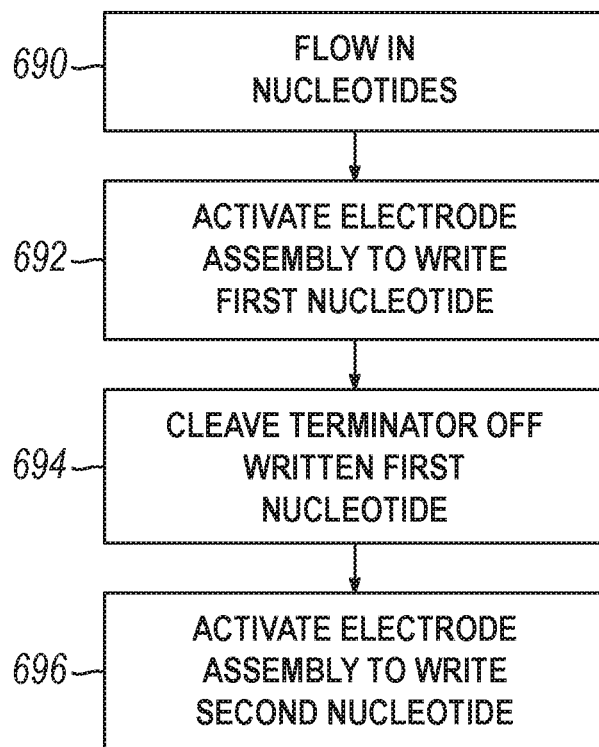
FIG. 8 depicts a flow chart of an example of a process for writing polynucleotides.

FIG. 8 shows an example of a process that may be utilized in the flow cell 600 to machine-write polynucleotides or other nucleotide sequences. At the beginning of the process, as shown in the first block 690 of FIG. 8, nucleotides may be flowed into the flow cell 600, over the wells 630. As shown in the next block 692 in FIG. 8, the electrode assembly 640 may then be activated to write a first nucleotide to a primer at the bottom of a targeted well 630. As shown in the next block 694 of FIG. 8, a terminator may then be cleaved off the first nucleotide that was just written in the targeted well 630. Various suitable ways in which a terminator may be cleaved off the first nucleotide will be apparent to those skilled in the art in view of the teachings herein. Once the terminator is cleaved off the first nucleotide, as shown in the next block 696 of FIG. 8, the electrode assembly 640 may be activated to write a second nucleotide to the first nucleotide. While not shown in FIG. 8, a terminator may be cleaved off the second nucleotide, then a third nucleotide may be written to the second nucleotide, and so on until the desired sequence of nucleotides has been written.

In some implementations, encoding of data via synthesis of biological materials such as DNA may be performed in other manners. For example, in some implementations, the flow cell 600 may lack the electrode assembly 640 altogether. For instance, deblock reagents may be selectively communicated from the flow channel 662 to the wells 630 through the openings 660. This may eliminate the need for electrode assemblies 640 to selectively activate nucleotides. As another example, an array of wells 630 may be exposed to a solution containing all nucleotide bases that may be used in encoding the data, and then individual nucleotides may be selectively activated for individual wells 630 by using light from a spatial light modulator (SLM). As another example, in some implementations individual bases may be assigned combined values (e.g., adenine may be used to encode the binary couplet 00, guanine may be used to encode the binary couplet 01, cytosine may be used to encode the binary couplet 10, and thymine may be used to encode the binary couplet 11) to increase the storage density of the polynucleotides being created. Other examples are also possible and will be immediately apparent to those skilled in the art in light of this disclosure. Accordingly, the above description of synthesizing biological materials such as DNA to encode data should be understood as being illustrative only; and should not be treated as limiting.

VI. Reading Machine-Written Biological Material

After polynucleotide strands 650 have been machine-written in one or more wells 630 of a flow cell 600, the polynucleotide strands 650 may be subsequently read to extract whatever data or other information was stored in the machine-written polynucleotide strands 650. Such a reading process may be carried out using an arrangement such as that shown in FIG. 5 and described above. In other words, one or more light sources 560 may be used to illuminate one or more fluorophores associated with the machine-written polynucleotide strands 650; and one or more image sensors 540 may be used to detect the fluorescent light emitted by the illuminated one or more fluorophores associated with the machine-written polynucleotide strands 650. The fluorescence profile of the light emitted by the illuminated one or more fluorophores associated with the machine-written polynucleotide strands 650 may be processed to determine the sequence of bases in the machine-written polynucleotide strands 650. This determined sequence of bases in the machine-written polynucleotide strands 650 may be processed to determine the data or other information that was stored in the machine-written polynucleotide strands 650.

In some versions, the machine-written polynucleotide strands 650 remain in the flow cell 600 containing wells 630 for a storage period. When it is desired to read the machine-written polynucleotide strands 650, the flow cell 600 may permit the machine-written polynucleotide strands 650 to be read directly from the flow cell. By way of example only, the flow cell 600 containing wells 630 may be received in a cartridge (e.g., cartridge 200) or base instrument 102 containing light sources 560 and/or image sensors 540, such that the machine-written polynucleotide strands 650 are read directly from the wells 630.

Figure 10:
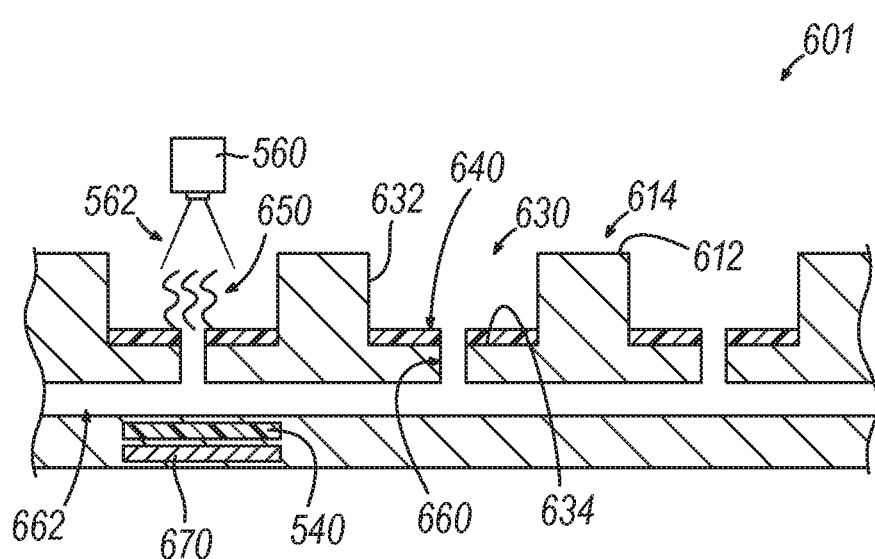
FIG. 10 depicts a block schematic cross-sectional view of another example of wells that may be incorporated into the channel of FIG. 4.

As another illustrative example, the flow cell containing wells 630 may directly incorporate one or both of light source(s) 560 or image sensor(s) 540. FIG. 10 shows an example of a flow cell 601 that includes wells 630 with electrode assemblies 640, one or more image sensors 540, and a control circuit 670. Like in the flow cell 500 depicted in FIG. 5, the flow cell 601 of this example is operable to receive light 562 projected from a light source 560. This projected light 562 may cause one or more fluorophores associated with the machine-written polynucleotide strands 650 to fluoresce; and the corresponding image sensor(s) 540 may capture the fluorescence emitted from the one or more fluorophores associated with the machine-written polynucleotide strands 650.

As noted above in the context of the flow cell 500, each well 650 of the flow cell 601 may include its own image sensor 540 and/or its own light source 560; or these components may be otherwise configured and arranged as described above. In the present example, the fluorescence emitted from the one or more fluorophores associated with the machine-written polynucleotide strands 650 may reach the image sensor 540 via the opening 660. In addition, or in the alternative, the electrode assembly 640 may comprise an optically transparent material (e.g., optically transparent conducting film (TCF), etc.), and the flow cell 601 itself may comprise an optically transparent material (e.g., glass), such that the electrode assembly 640 and the material forming the flow cell 601 may allow the fluorescence emitted from the one or more fluorophores associated with machine-written polynucleotide strands 650 to reach the image sensor 540. Moreover, various kinds of optical elements (e.g., lenses, optical waveguides, etc.) may be interposed between the wells 650 and the corresponding image sensor(s) to ensure that the image sensor 540 is only receiving fluorescence emitted from the one or more fluorophores associated with the machine-written polynucleotide strands 650 of the desired well(s) 630.

In the present example, the control circuit 670 is integrated directly into the flow cell 601. By way of example only, the control circuit 670 may comprise a CMOS chip and/or other printed circuit configurations/components. The control circuit 670 may be in communication with the image sensor(s) 540, the electrode assembly(ies) 640, and/or the light source 560. In this context, "in communication" means that the control circuit 670 is in electrical communication with image sensor(s) 540, the electrode assembly(ies) 640, and/or the light source 560. For instance, the control circuit 670 may be operable to receive and process signals from the image sensor(s) 540, with the signals representing images that are picked up by the image sensor(s) 540. "In communication" in this context may also include the control circuit 670 providing electrical power to the image sensor(s) 540, the electrode assembly(ies) 640, and/or the light source 560.

In some versions, each image sensor 540 has a corresponding control circuit 670. In some other versions, a control circuit 670 is coupled with several, if not all, of the image sensors in the flow cell 601. Various suitable components and configurations that may be used to achieve this will be apparent to those skilled in the art in view of the teachings herein. It should also be understood that the control circuit 670 may be integrated, in whole or in part, in a cartridge (e.g., removable cartridge 200) and/or in the base instrument 102, in addition to or in lieu of being integrated into the flow cell 601.

As still another illustrative example, regardless of whether a write-only flow cell like the flow cell 600 of FIG. 7 or a read-write flow cell like the flow cell 601 of FIG. 10 is used, the machine-written polynucleotide strands 650 may be transferred from wells 630 after being synthesized. This may occur shortly after the synthesis is complete, right before the machine-written polynucleotide strands 650 are to be read, or at any other suitable time. In such versions, the machine-written polynucleotide strands 650 may be transferred to a read-only flow cell like the flow cell 500 depicted in FIG. 5; and then be read in that read-only flow cell 500. Alternatively, any other suitable devices or processes may be used.

In some implementations, reading data encoded through the synthesis of biological materials may be achieved by determining the well(s) 630 storing the synthesized strand(s) 650 of interest and then sequencing those strands 650 using techniques such as those described previously (e.g., sequencing-by-synthesis). In some implementations, to facilitate reading data stored in nucleotide sequences, when data is stored, an index may be updated with information showing the well(s) 630 where the strand(s) 650 encoding that data was/were synthesized. For example, when an implementation of a system 100 configured to synthesize strands 650 capable of storing up to 256 bits of data is used to store a one megabit (1,048,576 bit) file, the system controller 120 may perform steps such as: 1) break the file into 4,096 256 bit segments; 2) identify a sequence of 4,096 wells 630 in the flow cell 600, 601 that were not currently being used to store data; 3) write the 4,096 segments to the 4,096 wells 430, 530; 4) update an index to indicate that the sequence starting with the first identified well 630 and ending at the last identified well 630 was being used to store the file. Subsequently, when a request to read the file was made, the index may be used to identify the well(s) 630 containing the relevant strand(s) 650, the strand(s) 650 from those wells 630 may be sequenced, and the sequences may be combined and converted into the appropriate encoding format (e.g., binary), and that combined and converted data may then be returned as a response to the read request.

In some implementations, reading of data previously encoded via synthesis of biological materials may be performed in other manners. For example, in some implementations, if a file corresponding to 4,096 wells 630 was to be written, rather than identifying 4,096 sequential wells 630 to write it to, a controller may identify 4,096 wells 630 and then update the index with multiple locations corresponding to the file in the event that those wells 630 did not form a continuous sequence. As another example, in some implementations, rather than identifying individual wells 630, a system controller 120 may group wells 630 together (e.g., into groups of 128 wells 630), thereby reducing the overhead associated with storing location data (i.e., by reducing the addressing requirements from one address per well 630 to one address per group of wells 630). As another example, in implementations that store data reflecting the location of wells 630 where DNA strands or other polynucleotides have been synthesized, that data may be stored in various ways, such as sequence identifiers (e.g., well 1, well 2, well 3, etc.) or coordinates (e.g., X and Y coordinates of a well's location in an array).

As another example, in some implementations, rather than reading strands 650 from the wells 630 in which they were synthesized, strands 650 may be read from other locations. For instance, strands 650 may be synthesized to include addresses, and then cleaved from the wells 630 and stored in a tube for later retrieval, during which the included address information may be used to identify the strands 650 corresponding to particular files. As another illustrative example, the strands 650 may be copied off the surface using polymerase and then eluted & stored in tube. Alternatively, the strands 650 may be copied on to a bead using biotinylated oligos hybridized to DNA strands or other polynucleotides and capturing extended products on streptavidin beads that are dispensed in the wells 630. Other examples are also possible and will be immediately apparent to those of skill in the art in light of this disclosure. Accordingly, the above description of retrieving data encoded through the synthesis of biological materials should be understood as being illustrative only; and should not be treated as limiting.

Implementations described herein may utilize a polymer coating for a surface of a flow cell, such as that described in U.S. Pat. No. 9,012,022, entitled "Polymer Coatings," issued Apr. 21, 2015, which is incorporated by reference herein in its entirety. Implementations described herein may utilize one or more labelled nucleotides having a detectable label and a cleavable linker, such as those described in U.S. Pat. No. 7,414,116, entitled "Labelled Nucleotide Strands," issued Aug. 19, 2008, which is incorporated by reference herein in its entirety. For instance, implementations described herein may utilize a cleavable linker that is cleavable with by contact with water-soluble phosphines or water-soluble transition metal-containing catalysts having a fluorophore as a detectable label. Implementations described herein may detect nucleotides of a polynucleotide using a two-channel detection method, such as that described in U.S. Pat. No. 9,453,258, entitled "Methods and Compositions for Nucleic Acid Sequencing," issued Sep. 27, 2016, which is incorporated by reference herein in its entirety. For instance, implementations described herein may utilize a fluorescent-based SBS method having a first nucleotide type detected in a first channel (e.g., dATP having a label that is detected in the first channel when excited by a first excitation wavelength), a second nucleotide type detected in a second channel (e.g., dCTP having a label that is detected in a second channel when excited by a second excitation wavelength), a third nucleotide type detected in both the first and second channel (e.g., dTTP having at least one label that is detected in both channels when excited by the first and/or second excitation wavelength), and a fourth nucleotide type that lacks a label that is not, or that is minimally, detected in either channel (e.g., dGTP having no label). Implementations of the cartridges and/or flow cells described herein may be constructed in accordance with one or more teachings described in U.S. Pat. No. 8,906,320, entitled "Biosensors for Biological or Chemical Analysis and Systems and Methods for Same," issued Dec. 9, 2014, which is incorporated by reference herein in its entirety; U.S. Pat. No. 9,512,422, entitled "Gel Patterned Surfaces," issued Dec. 6, 2016, which is incorporated by reference herein in its entirety; U.S. Pat. No. 10,254,225, entitled "Biosensors for Biological or Chemical Analysis and Methods of Manufacturing the Same," issued Apr. 9, 2019, which is incorporated by reference herein in its entirety; and/or U.S. Pub. No. 2018/0117587, entitled "Cartridge Assembly," published May 3, 2018, which is incorporated by reference herein in its entirety.

VII. Information Storage and Retrieval Using SBS Flow Cells

As previously indicated, "machine-written DNA" may be generated to index or otherwise track pre-existing DNA, to store data or information from any other source and for any suitable purpose, without necessarily requiring an intermediate conversion of raw data to a binary code. As also previously indicated, some implementations utilize sequencing by synthesis (SBS) for the read function, although certain aspects of this process may also be used to write certain indexing, cataloging, or other organizational information into DNA sequences or other polynucleotides. Generally, the SBS process is based on reversible dye-terminators that enable the identification of single bases as they are introduced into synthesized polynucleotides. SBS may be used for whole-genome and region sequencing, transcriptome analysis, metagenomics, small RNA discovery, methylation profiling, and genome-wide protein-nucleic acid interaction analysis. More specifically, SBS uses, in some instances, a number (e.g., four, three, two, one) of fluorescently labeled nucleotides to sequence tens of millions of clusters on a flow cell surface, in a massively parallel fashion. In other aspects, unlabeled nucleotides may be used. In other aspects, unlabeled nucleotides may be used. During each sequencing cycle, a single label deoxyribose nucleoside triphosphate (dNTP) is added to the nucleic acid chain. The nucleotide label serves as a "reversible terminator" for polymerization. After dNTP incorporation, the fluorescent dye is identified through laser excitation and imaging, and then enzymatically cleaved to allow the next round of incorporation. Base calls are made directly from signal intensity and/or color measurements during each cycle. The SBS workflow/process typically includes the following: (i) sample preparation; (ii) cluster generation; (iii) sequencing; and (iv) data analysis.

During sample (or library) preparation, the sequencing library is prepared by random fragmentation of a DNA or cDNA sample, which is then extracted and purified. After DNA purification the process may proceed with "tagmentation," during which transposases are used to randomly cut the purified DNA into short segments referred to as inserts or tags. Adapters (5' and 3') are then ligated on either side of the cut points and polynucleotides to which adapters have not been ligated are washed away. Once the adapters have been ligated to the tags, reduced cycle amplification is used to add additional motifs, such as sequencing primer binding sites, indices, barcodes, and regions (terminal sequences) that are complementary to oligos that are attached to the flow cell, and other kinds of molecular modifications that act as reference points during amplification, sequencing, and analysis. Indices and/or barcodes are unique DNA sequences ligated to fragments within a sequencing library for downstream in silico sorting and identification. During sequence analysis, a computer groups all reads with the same index together. Indices are typically a component of adapters or PCR primers and are ligated to the library fragments during the sequencing library preparation stage. Such indices are typically between 8-12 base pairs. Libraries with unique indexes may be pooled together, loaded into one lane of a sequencing flow cell, and sequenced in the same run. Reads are later identified and sorted using bioinformatic software. This process is referred to as "multiplexing."

Clustering is a process where each DNA fragment is locally amplified in an isothermal manner. During the cluster generation, the fragmented DNA library is loaded into a flow cell, such as any of the flow cells 400, 500, 600, 601 described herein. Each lane of the flow cell may be coated with a lawn of two types of surface-bound oligonucleotides (e.g. P5/P7 or P6/P8) which are complimentary to the library adapters, and the fragments of the DNA library are captured by these oligonucleotides. Hybridization is enabled by the first of the two types of oligos on the surface (e.g., P5 or P6). This oligonucleotide is complimentary to the adapter region on one of the DNA fragments and thus binds the DNA fragment. A DNA polymerase is then used to create a compliment of the hybridized DNA fragment. The newly formed double stranded DNA molecule is denatured, and the original template is washed away. The remaining polynucleotides are then clonally amplified through the bridge amplification process, during which each polynucleotide folds over and its adapter region hybridizes to the second type of oligo on the flow cell (e.g., P7 or P8). DNA polymerases are then used to generate the complimentary strand, forming a double-stranded bridge. This bridge is then denatured resulting in two single-stranded copies of the molecule tethered to the flow cell. The process is then repeated over and over and occurs simultaneously for millions of clusters resulting in clonal amplification of all the fragments in the DNA library. After bridge amplification, the reverse strands are cleaved and washed off, leaving only the forward strands. The 3' ends of these strands are then blocked to prevent unwanted priming. The clustering process may occur in an automated flow cell instrument (e.g., the base instrument 102) or in an onboard cluster module within a sequencing instrument. Each cluster may be defined as a clonal grouping of template DNA bound to the surface of a flow cell. As described, each cluster is seeded by a single template polynucleotide and is clonally amplified through bridge amplification until the cluster has about 1000 copies. Each cluster on a flow cell produces a single sequencing read. For example, 10,000 clusters on a flow cell may produce 10,000 single reads and 20,000 paired end reads. When cluster generation is complete, the DNA templates are ready for sequencing.

Sequencing begins with the extension of the first sequencing primer to produce the first read. With each cycle, four fluorescently tagged nucleotides (dNTPs) compete for addition to the growing chain. Only one dNTP is incorporated, based on the sequence of the template DNA. After the addition of each nucleotide, the clusters are excited by a light source and a characteristic fluorescent signal is emitted by fluorophores associated with the nucleotides. This is the process that is referred to as sequencing by synthesis or SBS. The number of cycles determines the length of the read. The emission wavelength, along with the signal intensity, determines the base call. For a given cluster, all identical strands are read simultaneously. Hundreds of millions of clusters are sequenced in a massively parallel process on the flow cell. After the completion of the first read, the read product is washed away. In this part of the process, the Index 1 read primer is introduced and hybridized to the template. The read is generated in a manner similar to the first read. After completion of the index read, the read product is washed off and the 3' end of the template is deprotected. The template then folds over and binds the second oligo on the flow cell. Index 2 is read in the same manner as Index 1. The Index 2 read product is washed off at the completion of this part of the process. Polymerases extend the second flow cell oligonucleotide, forming a double stranded bridge. This double stranded DNA is linearized and the 3' ends blocked. The original forward strand is cleaved off and washed away, leaving only the reverse strand. Read two begins with the introduction of the read two sequencing primer. As with read one, the sequencing parts of the process are repeated until the desired read length is achieved. The read two product is then washed away. This entire process generates millions of reads, representing all the fragments in the sequencing library. Because the sequencing process uses a reversible terminator-based method that detects single bases as they are incorporated into DNA template strands, and because all four reversible terminator-bound dNTPs are present during each sequencing cycle, natural competition may minimize incorporation bias and greatly reduce raw error rates. The result may be highly accurate base-by-base sequencing that virtually eliminates sequence context-specific errors, even within repetitive sequence regions and homopolymers.

During data analysis and alignment, sequences from pooled sample libraries are separated based on the unique indices introduced during sample preparation. For each sample, reads with similar stretches of base calls are locally clustered. Sequencing occurs for millions of clusters at once and, as previously stated, each cluster has about 1,000 identical copies of a DNA insert. A sequence "read" refers generally to the data string of A, T, C, and G bases corresponding to the sample DNA or RNA. Forward and reverse reads are paired creating contiguous sequences (referred to as "contigs"), which aligned back to a reference genome for variant identification. The reference genome is a fully sequenced and assembled genome that acts as a scaffold against which new sequence reads are aligned and compared. The paired-end information is used to resolve ambiguous alignments. Following alignment, many variations of analysis are possible such as, for example, single nucleotide polymorphism (SNP) or insertion-deletion (indel) identification, read counting for RNA methods, phylogenetic or metagenomic analysis.

It may be desirable to use flow cells, such as those described herein, to obtain and optionally catalogue sequences directly from biological samples. Flow cells may be used, not only for reading and writing, but for immobilizing macromolecules such as proteins and cells for recording of data. The flow cells may be used for cataloguing data based on interactions with biological molecules on the surface of the flow cell, and the data may be read-out directly on the same flow cell.

Figure 11:
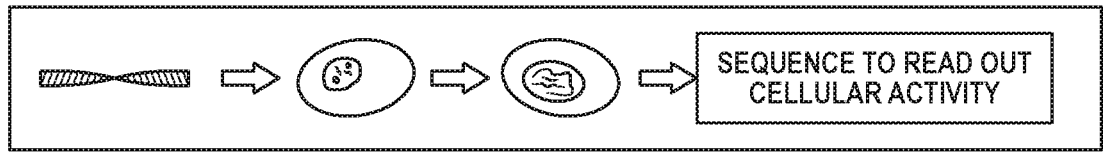
FIG. 11 depicts one example of a DNA-based cellular record, in which data may be incorporated into a cell for storage, wherein such data may later be accessed and sequenced to obtain the information.

In one example, the flow cell may be used as a "cell culture flow cell" in which the flow cell may be used as a culturing device and may be used store cells containing data. In this aspect, DNA of interest may be written, and then inserted into the genome of the cultured cells for storage and later reading. For example, electroporation methods may be used with the disclosed apparatus, in which an electrical pulse at a selected voltage may be discharged through a cell population, for example, a cell suspension, which disturbs the phospholipid bilayer of the membrane and results in temporary pores through which a polynucleotide may be driven across the membrane through the pores. Electrodes of the apparatus may be used to effect the electrical pulse for causing delivery of a polynucleotide into the cell. Localized electrodes may be used to selectively deliver nucleotides to certain cells within the flow cell. The cells in cell culture may be used as a storage medium for the inserted DNA, per FIG. 11.

Alternatively, the flow cell may be used to immobilize cells and the flow cell may be used to catalogue DNA sequences located on the surface of cells. The flow cells may further be used to catalogue proteins, create on-demand vaccines or to create a pathogen record, or may be used to store the DNA of a species on a chip, or may be used to creating a health record over time for an individual by flowing cells over the surface and recording data. Barcodes (unique, known sequences) may be added throughout the process for later retrieval and further cataloging, per FIG. 12.

In one aspect, the flow cells may be used to sequence the variable sections of an individual's immune cells while in a healthy state (e.g., before chemotherapy). The data may be written onto a flow cell for storage, and the data may be later used to restore an individual's immune system after it is lost (e.g., following chemotherapy) by inserting the healthy-state variable section into progenitor T or B cells to recreate the individual's immune system.

In one aspect, a method for one or both of recording and storing information from a biological sample is disclosed. In this aspect, the method may comprise contacting a biological sample with the apparatus of FIG. 1. In particular, the apparatus may comprise (a) a flow cell receiving portion 220 having one or more flow cell channels 410 and a plurality of wells 430, each flow cell channel 410 to receive a flow of fluid, each well of the plurality of wells being fluidically coupled with the corresponding flow cell channel 410, each well of the plurality of wells defining a corresponding depth; (b) a plurality of electrodes, each electrode of the plurality of electrodes being positioned in a corresponding well of the plurality of wells 430, the electrodes to effect one or both of reading or writing of a polynucleotide in the corresponding well; and (c) an imaging assembly to capture images indicative of a nucleotide in a polynucleotide written in the wells; wherein said contacting comprises contacting said biological sample with the flow cell body of said apparatus; and wherein said information is a DNA or RNA sequence contained within said biological sample.

In one aspect, the information that is being recorded and/or stored, may be selected from DNA, RNA, or both DNA and RNA from the biological sample. In this aspect, the polynucleotide of the apparatus may be complementary to the sequence of the DNA and/or RNA of the biological sample, which may be written from the biological sample, optionally stored for a period of time, and later read using the SBS methods as described herein. In one aspect, mRNA may be captured using the polyT oligo synthesized on a capture region. Similarly, targeted region capture probes may be synthesized for capturing specific regions and random sequences may be synthesized to capture non-specific DNA. In one aspect, the information being recorded and/or stored may include cell-free DNA and/or cell-free RNA, which may be obtained from a biological fluid outside the cell, which may be harvested and separated from the cell and flowed into the flow cell 220 for writing of said DNA and/or RNA data, for optional storage and later retrieval The biological sample may include, for example, any source of such information, including but not limited to whole blood, serum, plasma, or combinations thereof.

In one aspect, the information that is being recorded and/or stored, may be obtained from a biological sample that includes a pathogen selected virus and/or a bacteria. For example, information in the form of a nucleotide sequence may be obtained and stored and later retrieved by introducing a pathogen into a flow cell channel 410 and writing the DNA from the pathogen in the wells 430, 630. In this aspect, the pathogen may be processed prior to introduction into the wells 430, 630 to better expose the DNA and/or RNA to be written to the wells 430, 630. For example, in the case of a virus, a biological sample may be subjected to processing sufficient to provide disruption of a capsid coating sufficient to allow exposure of the DNA/RNA of the virus for writing to the surface or for sequencing of the DNA/RNA of the virus.

Similarly, as with any cell introduced into the flow cell 400, 500, 600, 601 for writing/reading of information, said cell may be lysed prior to introduction into the flow cell 400, 500, 600, 601 such that the DNA/RNA of interest may be exposed for sequencing, whether for writing or reading of the DNA/RNA of interest. In one aspect, cells may be lysed in-situ using, for example, heat or light activated lysis reagents to maintain the spatial confinement of the released molecules within the capture region. Alternatively, the electrode assembly 640 may be used to generate lysis conditions, for example, a pH change in combination with heat and/or a lysis buffer. In a further aspect, select regions of a pathogen may be written to the flow cell using CRISPR methods. In this aspect, the apparatus may be used as a pathogen monitoring system that may also be used to manufacture DNA vaccines against a pathogen written to the flow cell.

The information that is being recorded and/or stored may further benefit from the introduction of a location indexing feature. For example, a location indexing feature may be used to identify the location of said information on the flow cell 400, 500, 600, 601 itself. Such a location indexing feature may be affixed to the flow cell 400, 500, 600, 601, for example, at particular wells 430, 530, 630 or flow cell channels 410, and may allow for later identification of the information stored in any particular well 430, 530, 630 or flow cell channel 410.

In a further aspect, the information that is being recorded and/or stored, may further comprise a source indexing feature. The source indexing feature may, for example, be used to identify the source of information on said flow cell 400, 500, 600, 601. That is, in comparison to the location feature, above, which allows for identifying the location of the stored information, the source indexing feature may include a unique sequence that is incorporated into the written and/or read (via SBS methods) that identifies the source of the information. For example, a sample from a particular patient may be written or sequenced to include a unique nucleotide identifier that provides a source indexing feature that may further be used for separating nucleotide sequences of interest from a population of sequences.

In one aspect, it may be desirable to first select a population of cells from which recording and/or storing of information is desired. In this aspect, the contacting part of the process may include contacting a biological sample with the flow cell 400, 500, 600, 601 sufficient to cause binding of a predetermined binding component that is selective for a particular cell type. In this aspect, the binding event causes only the cells of interest to bind to the well 430, 530, 630, sufficient to affix, (temporarily or permanently) the biological cell to the well 430, 530, 630. The binding component may be any component that binds to a surface molecule or surface feature of the biological cell of interest, and may include, for example, a protein, a peptide, a receptor, a sugar molecule, or combinations thereof. In certain aspects, the binding component may be selected from a nucleotide, an oligonucleotide, a polynucleotide, a protein, a peptide, a polypeptide, a small molecule, aptamers, cell permeable polymers such as phospholipids, and combinations thereof. Following the binding part of the process, the information (in the form of DNA or RNA, for example) may then be obtained from the biological cell. This may be useful, for example, for the detection of RNA expression in response to binding to a drug, wherein the binding feature is a small molecule (drug) of interest, which binding to a receptor on the cell (biological cell of interest) and the biological information in the form of mRNA may be written and or read to determine changes in protein expression in response to binding to the drug of interest.

Figure 12:
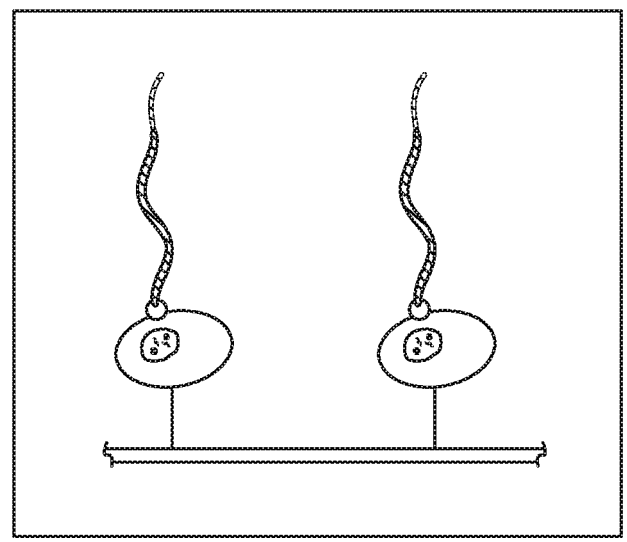
FIG. 12 depicts an example of a cell-based system suitable for high throughput target/drug screening in which cells are affixed to a flow cell, in which the cells may display a protein of interest and which further contains a DNA barcode.

In a further aspect, the cell population may include either all cell types or a population of interest, which may be bound to the well 430, 530, 630, and which may then be exposed to a molecule of interest via the flow cell channel 410. Bound molecules of interest, which may optionally include an oligonucleotide tag, may then be detected. (FIG. 12). Cell types may include cells obtained from any biological sample containing the biological cells of interest. Biological samples may include, for example, whole blood, serum, plasma, or combinations thereof.

In a further aspect, it may be desirable to treat a biological sample after it has been flowed through the flow cell channel 410, for example, by flowing in a sample containing biological cells, then contacting the well 430, 530, 630 with a first solution sufficient to separate non-affixed cells from flow-cell affixed cells. Following this part of the process, which serves as a wash part of the process, the affixed cells may be better used for reading/writing of data, or for contacting with molecules of interest for further characterization of the affixed cell population. In one aspect, the well 430, 530, 630 may be contacted with a second solution sufficient to lyse the well-affixed cells. This process may be used, for example, to expose and prepare one or both of DNA and RNA for reading and/or writing of the nucleotide data. The method may further comprise flowing in a fluid that has a pH, isotonicity, and nutrients that are compatible with storage of the biological cells affixed to the well 430, 530, 630, for example, a culture medium as is known and used in the art for cell storage.

In a further aspect, the apparatus and methods disclosed herein may be used for the storage of a health record over time for an individual over time. In this aspect, the method may include obtaining the biological information of an individual according to any method as set forth above, for example, using read/write methods as described. The read/write methods may be repeated over time, at predetermined intervals, such that a record over time is created. Such record may allow determination of changes of cellular behavior over time, for example, over a period of months or years, and may be used, for example, to determine responses to external factors, for example treatment with a particular therapeutic or following exposure to an event that is predicted to have an effect on health, and in turn, cellular activity or composition.

Likewise, the disclosed apparatus and methods may be used for the storing of biological information for a species. In this manner, the method may comprise obtaining the biological information of a species according to the method as described herein. Such information may include, for example, sequence diversity or consensus sequences.

In a yet further aspect, the methods may be used for the cataloging of immune system information from an individual. DNA and/or RNA may be analyzed using the disclosed methods to determine the regions that encode heavy chain immunoglobulins (IgH), each of which chain is composed of a constant (C) and a variable region. For the heavy chain, the variable region is composed of a variable (V), diversity (D), and joining (J) segments. Several distinct sequences coding for each type of these segments are present in the genome. A specific variable-diversity-joining ("VDJ") recombination event occurs during the development of a B-cell, marking that cell to generate a specific heavy chain. Somatic mutation often occurs close to the site of the recombination, causing the addition or deletion of several nucleotides, further increasing the diversity of heavy chains generated by B-cells. The possible diversity of the antibodies generated by a B-cell is then the product of the different heavy and light chains. The variable regions of the heavy and light chains contribute to form the antigen recognition (or binding) region or site.

Added to this diversity is a process of somatic hypermutation which may occur after a specific response is mounted against some epitope. Immune system information may be measured by reference to clonotypes which are determined from assessment of information available from the lymphocytes of an individual, a cell type which provides immune system information. Clonotypes are described in, for example, U.S. Pub. No. 2014/0342360, entitled "Method of Measuring Immune Activation," published Nov. 20, 2014, which is incorporated by reference herein in its entirety; and Yassai, Maryam B et al. "A Clonotype Nomenclature for T Cell Receptors." Immunogenetics vol. 61, 7 (2009): 493-502. doi:10.1007/s00251-009-0383-x, which is incorporated by reference herein in its entirety. Clonotype profiles may be generated from a sample of nucleic acids extracted from a sample containing B cells. B-cells include, for example, plasma B cells, memory B cells, B1 cells, B2 cells, marginal-zone B cells, and follicular B cells. B-cells may express immunoglobulins (antibodies, B cell receptor). Clonotypes may be constructed from sequence reads of nucleotides encoding immunoglobulin heavy chains (IgHs). In particular, clonotypes may be defined by a portion of a VDJ encoding region and a portion of its associated constant region (or C region). An isotype may be determined from the nucleotide sequence encoding the portion of the C region, which may be adjacent to the VDJ encoding region. C-region encoding portions may be captured during amplification of IgH-encoding sequences.

In this aspect, the biological information obtained from the biological sample of an individual comprises the data contained within the immune system of the individual. For example, the biological sample used in conjunction with the methods and apparatus described herein may contain lymphocytes from the individual. Further, a clonotype profile may be obtained, stored, and optionally later accessed from the flow cell. In this aspect, a clonotype profile may comprise at least a portion of a VDJ region of a B cell receptor or at least a portion of a C gene segment from said individual. In other aspects, the clonotype profile may include one or more regions selected from a portion of a C gene segment of a B cell receptor, a VDJ region of a B cell receptor, and combinations thereof. The flow cell 400, 500, 600, 601 may contain one or more primers to amplify a clonotype of said individual. The primers may be used to amplify a region selected from a variable (V) region, a constant (C) region, a diversity (D) region, a joining (J) region, and combinations thereof. The flow cell 400, 500, 600, 601 may then be used to catalogue VDJ information from said immune cells of said individual, particularly before an immune-system depleting event such as chemotherapy. The immune system information stored in the flow cell 400, 500, 600, 601 may later be used to restore the immune system of the individual after an immune-system depleting event.

In a further aspect, the read/write methods disclosed herein, the described apparatus may be used to create a vaccine composition. For example, a viral pathogen may be contacted with a flow cell 400, 500, 600, 601 comprising primers to bind to the viral pathogen. The nucleotide sequence of the viral pathogen may be written to the well 430, 530, 630 of a flow cell 400, 500, 600, 601; and the viral pathogen information may thus be stored in the flow cell 400, 500, 600, 601. By reading the viral pathogen from the flow cell 400, 500, 600, 601, viral fragments may be generated, which may then be used to form a vaccine composition.

VIII. Miscellaneous

All of the references, including patents, patent applications, and articles, are explicitly incorporated by reference herein in their entirety.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

As used herein, an element or step recited in the singular and proceeded with the word "a" or "an" should be understood as not excluding plural of said elements or steps, unless such exclusion is explicitly stated. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this Specification are used to describe and account for small fluctuations, such as due to variations in processing. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

There may be many other ways to implement the subject technology. Various functions and elements described herein may be partitioned differently from those shown without departing from the scope of the subject technology. Various modifications to these implementations may be readily apparent to those skilled in the art, and generic principles defined herein may be applied to other implementations. Thus, many changes and modifications may be made to the subject technology, by one having ordinary skill in the art, without departing from the scope of the subject technology. For instance, different numbers of a given module or unit may be employed, a different type or types of a given module or unit may be employed, a given module or unit may be added, or a given module or unit may be omitted.

Underlined and/or italicized headings and subheadings are used for convenience only, do not limit the subject technology, and are not referred to in connection with the interpretation of the description of the subject technology. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A method comprising:
  contacting a biological sample with an apparatus, the apparatus comprising:
    (a) a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth,
  (b) a plurality of electrodes, each electrode of the plurality of electrodes being positioned in a corresponding well of the plurality of wells, the plurality of electrodes to effect one or both of reading or writing of a polynucleotide in the corresponding well of the plurality of wells, and
  (c) an imaging assembly to capture images indicative of the nucleotide in a polynucleotide written in at least one well of the plurality of wells;
obtaining information by one or both of reading or writing of said polynucleotide;
wherein said contacting comprises contacting said biological sample with the flow cell body of said apparatus;
wherein said information is a DNA or RNA sequence contained within said biological sample;
the method further comprising:
  storing said obtained information on or in a biological cell; and
  storing said biological cell with said obtained information stored on or in the biological cell.

2. The method of claim 1 wherein said information is selected from one or both of a DNA sequence from said biological sample and an RNA sequence from said biological sample, and wherein said polynucleotide corresponds to said one or both of said DNA sequence of said biological sample and said RNA sequence from said biological sample.

3. The method of claim 2 wherein said one or both of RNA and DNA are cell-free DNA or cell-free RNA.

4. The method of claim 1, wherein said biological sample is selected from whole blood, serum, plasma, or combinations thereof.

5. The method of claim 1, wherein said biological sample is selected from one or both of a virus and a bacteria.

6. The method of claim 1, further comprising incorporating a location indexing feature, wherein said location indexing feature to identify the location of said information on said apparatus.

7. The method of claim 6, wherein said location indexing feature comprises a predetermined sequence affixed to said apparatus wherein said predetermined sequence is incorporated into said polynucleotide.

8. The method of claim 1, further comprising incorporating a source indexing feature, wherein said source indexing feature is to identify the source of said information on said apparatus.

9. The method of claim 8, wherein said source indexing feature comprises a predetermined sequence that is incorporated into said polynucleotide.

10. A method comprising:
  contacting a biological sample with an apparatus, the apparatus comprising:
    (a) a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth,
    (b) a plurality of electrodes, each electrode of the plurality of electrodes being positioned in a corresponding well of the plurality of wells, the plurality of electrodes to effect one or both of reading and writing of a polynucleotide in the corresponding well of the plurality of wells,
    (c) an imaging assembly to capture images indicative of the nucleotide in a polynucleotide written in at least one well of the plurality of wells, and
    (d) one or more binding components positioned in or approximate to the plurality of wells, the one or more binding components to selectively bind with a first biological cell in said biological sample;
  wherein said contacting comprises contacting said biological sample with the flow cell body of said apparatus to bind said binding component with said first biological cell, wherein said binding affixes said first biological cell to said apparatus;
the method further comprising:
  extracting information from first biological cell within the apparatus, the extracted information including one or more polynucleotides; and
  storing the extracted information on or in a second biological cell.

11. The method of claim 10, wherein said binding component is to bind to a preselected cell type, wherein said binding component is selective for said preselected cell type.

12. The method of claim 11, wherein said binding component binds to a surface molecule of said biological cell, wherein said surface molecule is selected from a protein, a peptide, a receptor, a sugar molecule, or combinations thereof.

13. The method of claim 11, wherein said binding component is selected from a nucleotide, a protein, a peptide, a small molecule, or combinations thereof.

14. The method of claim 10, wherein said biological sample is selected from whole blood, serum, plasma, or combinations thereof.

15. The method of claim 10, further comprising contacting said apparatus with a first solution sufficient to separate non-affixed cells from and apparatus-affixed cells.

16. The method of claim 15, further comprising contacting said apparatus with a second solution sufficient to lyse flow-cell affixed cells, wherein said lysing exposes one or both of DNA and RNA for writing of said polynucleotide contained within said apparatus-affixed cells.

17. The method of claim 10, further comprising binding a plurality of biological cells in said apparatus and flowing in a fluid for storage of said plurality of biological cells.

18. The method of claim 17 wherein said fluid for storage is a culture medium.

19. The method of claim 10, further comprising reading said information in said polynucleotide.

20. The method of claim 1, the step of storing said information on or in the biological cell comprising activating one or more electrodes of the plurality of electrodes to deliver the DNA or RNA sequence into the biological cell.

21. A method of operating an apparatus, the apparatus comprising:
  (a) a flow cell body defining one or more flow channels and a plurality of wells, each flow channel of the one or more flow channels to receive a flow of fluid, each well of the plurality of wells being fluidically coupled with the corresponding flow channel of the one or more flow channels, each well of the plurality of wells defining a corresponding depth,
  (b) a plurality of electrodes, each electrode of the plurality of electrodes being positioned in a corresponding well of the plurality of wells, the plurality of electrodes to effect one or both of reading or writing of a polynucleotide in the corresponding well of the plurality of wells, and (c) an imaging assembly to capture images indicative of the nucleotide in a polynucleotide written in at least one well of the plurality of wells;

the method comprising:

contacting a biological sample with the apparatus;

obtaining information from the biological sample via the apparatus, the obtaining information including one or more polynucleotide sequences of the biological sample;

storing the obtained information on or in a biological cell via the apparatus; and storing the biological cell with the obtained information stored on or in the biological cell.

* * * * *

UNITED STATES PATENT AND TRADEMARK OFFICE
CERTIFICATE OF CORRECTION

| | |
|---|---|
| PATENT NO. | : 11,835,510 B2 |
| APPLICATION NO. | : 17/470228 |
| DATED | : December 5, 2023 |
| INVENTOR(S) | : Tarun Khurana et al. |

It is certified that error appears in the above-identified patent and that said Letters Patent is hereby corrected as shown below:

On the Title Page

Item (72) Inventors, in Column 1, Line 1, delete "Freemont" and insert -- Fremont --, therefor.

Signed and Sealed this
Twenty-seventh Day of February, 2024

Katherine Kelly Vidal
*Director of the United States Patent and Trademark Office*